US012592306B2

(12) United States Patent
Zade et al.

(10) Patent No.: US 12,592,306 B2
(45) Date of Patent: Mar. 31, 2026

(54) DEVICES AND METHODS FOR INITIALIZATION OF DRUG DELIVERY DEVICES USING MEASURED ANALYTE SENSOR INFORMATION

(71) Applicant: Insulet Corporation, Acton, MA (US)

(72) Inventors: Ashutosh Zade, San Diego, CA (US); Joon Bok Lee, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 855 days.

(21) Appl. No.: 17/730,839

(22) Filed: Apr. 27, 2022

(65) Prior Publication Data

US 2022/0347386 A1 Nov. 3, 2022

Related U.S. Application Data

(60) Provisional application No. 63/180,777, filed on Apr. 28, 2021.

(51) Int. Cl.
*G16H 20/17* (2018.01)
*A61M 5/172* (2006.01)
(Continued)

(52) U.S. Cl.
CPC .......... *G16H 20/17* (2018.01); *A61M 5/1723* (2013.01); *G16H 20/13* (2018.01); *G16H 40/67* (2018.01);
(Continued)

(58) Field of Classification Search
CPC ... A61B 5/14532; A61B 5/4839; A61B 5/145; A61B 5/14865; A61B 5/7275;
(Continued)

(56) References Cited

U.S. PATENT DOCUMENTS 303,013 A 8/1884 Horton
2,797,149 A 6/1957 Skeggs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Wesley G Harris
(74) *Attorney, Agent, or Firm* — Goodwin Procter LLP

(57) ABSTRACT

Disclosed are processes and techniques implementable by a drug delivery system to maintain optimal drug delivery for a patient according to a treatment plan. The disclosed techniques enable a new drug delivery device that is exchanged for a previous drug delivery device to operate using analyte-based drug delivery control immediately during initialization instead of having to wait for a warm-up period. For example, a drug delivery device may include a processor and a memory storing instructions that, when executed by the processor, operate the drug delivery device to receive a present analyte measurement value from an analyte sensor during an initialization of the drug delivery device, receive backfill values measured by the analyte sensor prior to the initialization, calculate a dosage of a drug using the present analyte measurement value and the backfill values, and deliver the dosage of the drug. Other embodiments are described.

16 Claims, 6 Drawing Sheets

(51) Int. Cl.

| | | |
|---|---|---|
| *G16H 20/13* | (2018.01) | |
| *G16H 40/67* | (2018.01) | |
| *G16H 50/20* | (2018.01) | |
| *G16H 50/50* | (2018.01) | |

(52) U.S. Cl.

CPC ............. *G16H 50/20* (2018.01); *G16H 50/50*
(2018.01); *A61M 2205/52* (2013.01); *A61M 2230/201* (2013.01)

(58) Field of Classification Search

CPC .. A61B 5/14503; A61B 5/486; A61M 5/1723;
A61M 2230/201; A61M 2005/14208;
A61M 2005/1726; A61M 2230/00; A61M
2230/20; A61M 5/14244; A61M
2205/3303; G16H 20/17; G16H 20/13;
G16H 40/67; G16H 50/20; G16H 50/50;
G16H 20/00; G16H 20/10

See application file for complete search history.

(56) References Cited

U.S. PATENT DOCUMENTS

| | | | |
|---|---|---|---|
| 3,631,847 A | 1/1972 | Hobbs | |
| 3,634,039 A | 1/1972 | Brondy | |
| 3,812,843 A | 5/1974 | Wootten et al. | |
| 3,841,328 A | 10/1974 | Jensen | |
| 3,963,380 A | 6/1976 | Thomas, Jr. et al. | |
| 4,055,175 A | 10/1977 | Clemens et al. | |
| 4,146,029 A | 3/1979 | Ellinwood, Jr. | |
| 4,151,845 A | 5/1979 | Clemens | |
| 4,245,634 A | 1/1981 | Albisser et al. | |
| 4,368,980 A | 1/1983 | Aldred et al. | |
| 4,373,527 A | 2/1983 | Fischell | |
| 4,403,984 A | 9/1983 | Ash et al. | |
| 4,464,170 A | 8/1984 | Clemens et al. | |
| 4,469,481 A | 9/1984 | Kobayashi | |
| 4,475,901 A | 10/1984 | Kraegen et al. | |
| 4,526,568 A | 7/1985 | Clemens et al. | |
| 4,526,569 A | 7/1985 | Bernardi | |
| 4,529,401 A | 7/1985 | Leslie et al. | |
| 4,559,033 A | 12/1985 | Stephen et al. | |
| 4,559,037 A | 12/1985 | Franetzki et al. | |
| 4,573,968 A | 3/1986 | Parker | |
| 4,624,661 A | 11/1986 | Arimond | |
| 4,633,878 A | 1/1987 | Bombardieri | |
| 4,657,529 A | 4/1987 | Prince et al. | |
| 4,685,903 A | 8/1987 | Cable et al. | |
| 4,731,726 A | 3/1988 | Allen, III | |
| 4,743,243 A | 5/1988 | Vaillancourt | |
| 4,755,173 A | 7/1988 | Konopka et al. | |
| 4,781,688 A | 11/1988 | Thoma et al. | |
| 4,781,693 A | 11/1988 | Martinez et al. | |
| 4,808,161 A | 2/1989 | Kamen | |
| 4,854,170 A | 8/1989 | Brimhall et al. | |
| 4,886,499 A | 12/1989 | Cirelli et al. | |
| 4,900,292 A | 2/1990 | Berry et al. | |
| 4,919,596 A | 4/1990 | Slate et al. | |
| 4,925,444 A | 5/1990 | Orkin et al. | |
| 4,940,527 A | 7/1990 | Kazlauskas et al. | |
| 4,975,581 A | 12/1990 | Robinson et al. | |
| 4,976,720 A | 12/1990 | Machold et al. | |
| 4,981,140 A | 1/1991 | Wyatt | |
| 4,994,047 A | 2/1991 | Walker et al. | |
| 5,007,286 A | 4/1991 | Malcolm et al. | |
| 5,097,834 A | 3/1992 | Skrabal | |
| 5,102,406 A | 4/1992 | Arnold | |
| 5,109,850 A | 5/1992 | Blanco et al. | |
| 5,125,415 A | 6/1992 | Bell | |
| 5,134,079 A | 7/1992 | Cusack et al. | |
| 5,153,827 A | 10/1992 | Coutre et al. | |
| 5,165,406 A | 11/1992 | Wong | |
| 5,176,662 A | 1/1993 | Bartholomew et al. | |
| 5,178,609 A | 1/1993 | Ishikawa | |
| 5,207,642 A | 5/1993 | Orkin et al. | |
| 5,232,439 A | 8/1993 | Campbell et al. | |
| 5,237,993 A | 8/1993 | Skrabal | |
| 5,244,463 A | 9/1993 | Cordner, Jr. et al. | |
| 5,257,980 A | 11/1993 | Van Antwerp et al. | |
| 5,273,517 A | 12/1993 | Barone et al. | |
| 5,281,808 A | 1/1994 | Kunkel | |
| 5,299,571 A | 4/1994 | Mastrototaro | |
| 5,308,982 A | 5/1994 | Ivaldi et al. | |
| 5,342,298 A | 8/1994 | Michaels et al. | |
| 5,377,674 A | 1/1995 | Kuestner | |
| 5,380,665 A | 1/1995 | Cusack et al. | |
| 5,385,539 A | 1/1995 | Maynard | |
| 5,389,078 A | 2/1995 | Zalesky | |
| 5,411,889 A | 5/1995 | Hoots et al. | |
| 5,421,812 A | 6/1995 | Langley et al. | |
| 5,468,727 A | 11/1995 | Phillips et al. | |
| 5,505,709 A | 4/1996 | Funderburk et al. | |
| 5,505,828 A | 4/1996 | Wong et al. | |
| 5,507,288 A | 4/1996 | Bocker et al. | |
| 5,533,389 A | 7/1996 | Kamen et al. | |
| 5,558,640 A | 9/1996 | Pfeiler et al. | |
| 5,569,186 A | 10/1996 | Lord et al. | |
| 5,584,813 A | 12/1996 | Livingston et al. | |
| 5,609,572 A | 3/1997 | Lang | |
| 5,665,065 A | 9/1997 | Colman et al. | |
| 5,678,539 A | 10/1997 | Schubert et al. | |
| 5,685,844 A | 11/1997 | Marttila | |
| 5,685,859 A | 11/1997 | Kornerup | |
| 5,693,018 A | 12/1997 | Kriesel et al. | |
| 5,697,899 A | 12/1997 | Hillman et al. | |
| 5,700,695 A | 12/1997 | Yassinzadeh et al. | |
| 5,703,364 A | 12/1997 | Rosenthal | |
| 5,714,123 A | 2/1998 | Sohrab | |
| 5,716,343 A | 2/1998 | Kriesel et al. | |
| 5,722,397 A | 3/1998 | Eppstein | |
| 5,741,228 A | 4/1998 | Lambrecht et al. | |
| 5,746,217 A | 5/1998 | Erickson et al. | |
| 5,755,682 A | 5/1998 | Knudson et al. | |
| 5,758,643 A | 6/1998 | Wong et al. | |
| 5,800,405 A | 9/1998 | McPhee | |
| 5,800,420 A | 9/1998 | Gross et al. | |
| 5,801,057 A | 9/1998 | Smart et al. | |
| 5,804,048 A | 9/1998 | Wong et al. | |
| 5,817,007 A | 10/1998 | Fodgaard et al. | |
| 5,820,622 A | 10/1998 | Gross et al. | |
| 5,823,951 A | 10/1998 | Messerschmidt | |
| 5,840,020 A | 11/1998 | Heinonen et al. | |
| 5,848,991 A | 12/1998 | Gross et al. | |
| 5,851,197 A | 12/1998 | Marano et al. | |
| 5,858,005 A | 1/1999 | Kriesel | |
| 5,865,806 A | 2/1999 | Howell | |
| 5,871,470 A | 2/1999 | McWha | |
| 5,879,310 A | 3/1999 | Sopp et al. | |
| 5,902,253 A | 5/1999 | Pfeiffer et al. | |
| 5,931,814 A | 8/1999 | Alex et al. | |
| 5,932,175 A | 8/1999 | Knute et al. | |
| 5,935,099 A | 8/1999 | Peterson et al. | |
| 5,947,911 A | 9/1999 | Wong et al. | |
| 5,971,941 A | 10/1999 | Simons et al. | |
| 5,993,423 A | 11/1999 | Choi | |
| 5,997,501 A | 12/1999 | Gross et al. | |
| 6,017,318 A | 1/2000 | Gauthier et al. | |
| 6,024,539 A | 2/2000 | Blomquist | |
| 6,032,059 A | 2/2000 | Henning et al. | |
| 6,036,924 A | 3/2000 | Simons et al. | |
| 6,040,578 A | 3/2000 | Malin et al. | |
| 6,049,727 A | 4/2000 | Crothall | |
| 6,050,978 A | 4/2000 | Orr et al. | |
| 6,058,934 A | 5/2000 | Sullivan | |
| 6,066,103 A | 5/2000 | Duchon et al. | |
| 6,071,292 A | 6/2000 | Makower et al. | |
| 6,072,180 A | 6/2000 | Kramer et al. | |
| 6,077,055 A | 6/2000 | Vilks | |
| 6,090,092 A | 7/2000 | Fowles et al. | |
| 6,101,406 A | 8/2000 | Hacker et al. | |
| 6,102,872 A | 8/2000 | Doneen et al. | |
| 6,115,673 A | 9/2000 | Malin et al. | |
| 6,123,827 A | 9/2000 | Wong et al. | |
| 6,124,134 A | 9/2000 | Stark | |

(56)　　　　　References Cited

U.S. PATENT DOCUMENTS

| | | | |
|---|---|---|---|
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,157,041 | A | 12/2000 | Thomas et al. |
| 6,161,028 | A | 12/2000 | Braig et al. |
| 6,162,639 | A | 12/2000 | Douglas |
| 6,196,046 | B1 | 3/2001 | Braig et al. |
| 6,200,287 | B1 | 3/2001 | Keller et al. |
| 6,200,338 | B1 | 3/2001 | Solomon et al. |
| 6,214,629 | B1 | 4/2001 | Freitag et al. |
| 6,226,082 | B1 | 5/2001 | Roe |
| 6,244,776 | B1 | 6/2001 | Wiley |
| 6,261,065 | B1 | 7/2001 | Nayak et al. |
| 6,262,798 | B1 | 7/2001 | Shepherd et al. |
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kunstner |
| 6,309,370 | B1 | 10/2001 | Haim et al. |
| 6,312,888 | B1 | 11/2001 | Wong et al. |
| 6,334,851 | B1 | 1/2002 | Hayes et al. |
| 6,375,627 | B1 | 4/2002 | Mauze et al. |
| 6,379,301 | B1 | 4/2002 | Worthington et al. |
| 6,402,689 | B1 | 6/2002 | Scarantino et al. |
| 6,470,279 | B1 | 10/2002 | Samsoondar |
| 6,475,196 | B1 | 11/2002 | Vachon |
| 6,477,901 | B1 | 11/2002 | Tadigadapa et al. |
| 6,484,044 | B1 | 11/2002 | Lilienfeld-Toal |
| 6,491,656 | B1 | 12/2002 | Morris |
| 6,512,937 | B2 | 1/2003 | Blank et al. |
| 6,525,509 | B1 | 2/2003 | Petersson et al. |
| 6,528,809 | B1 | 3/2003 | Thomas et al. |
| 6,540,672 | B1 | 4/2003 | Simonsen et al. |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,553,841 | B1 | 4/2003 | Blouch |
| 6,554,798 | B1 | 4/2003 | Mann et al. |
| 6,556,850 | B1 | 4/2003 | Braig et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,562,014 | B2 | 5/2003 | Lin et al. |
| 6,569,125 | B2 | 5/2003 | Jepson et al. |
| 6,572,542 | B1 | 6/2003 | Houben et al. |
| 6,572,545 | B2 | 6/2003 | Knobbe et al. |
| 6,574,490 | B2 | 6/2003 | Abbink et al. |
| 6,575,905 | B2 | 6/2003 | Knobbe et al. |
| 6,580,934 | B1 | 6/2003 | Braig et al. |
| 6,618,603 | B2 | 9/2003 | Varalli et al. |
| 6,633,772 | B2 | 10/2003 | Ford et al. |
| 6,645,142 | B2 | 11/2003 | Braig et al. |
| 6,653,091 | B1 | 11/2003 | Dunn et al. |
| 6,662,030 | B2 | 12/2003 | Khalil et al. |
| 6,669,663 | B1 | 12/2003 | Thompson |
| 6,678,542 | B2 | 1/2004 | Braig et al. |
| 6,699,221 | B2 | 3/2004 | Vaillancourt |
| 6,718,189 | B2 | 4/2004 | Rohrscheib et al. |
| 6,721,582 | B2 | 4/2004 | Trepagnier et al. |
| 6,728,560 | B2 | 4/2004 | Kollias et al. |
| 6,740,059 | B2 | 5/2004 | Flaherty |
| 6,740,072 | B2 | 5/2004 | Starkweather et al. |
| 6,751,490 | B2 | 6/2004 | Esenaliev et al. |
| 6,758,835 | B2 | 7/2004 | Close et al. |
| 6,780,156 | B2 | 8/2004 | Haueter et al. |
| 6,810,290 | B2 | 10/2004 | Lebel et al. |
| 6,837,858 | B2 | 1/2005 | Cunningham et al. |
| 6,837,988 | B2 | 1/2005 | Leong et al. |
| 6,846,288 | B2 | 1/2005 | Nagar et al. |
| 6,862,534 | B2 | 3/2005 | Sterling et al. |
| 6,865,408 | B1 | 3/2005 | Abbink et al. |
| 6,890,291 | B2 | 5/2005 | Robinson et al. |
| 6,936,029 | B2 | 8/2005 | Mann et al. |
| 6,949,081 | B1 | 9/2005 | Chance |
| 6,958,809 | B2 | 10/2005 | Sterling et al. |
| 6,989,891 | B2 | 1/2006 | Braig et al. |
| 6,990,366 | B2 | 1/2006 | Say et al. |
| 7,008,404 | B2 | 3/2006 | Nakajima |
| 7,009,180 | B2 | 3/2006 | Sterling et al. |
| 7,016,713 | B2 | 3/2006 | Gardner et al. |
| 7,018,360 | B2 | 3/2006 | Flaherty et al. |
| 7,025,743 | B2 | 4/2006 | Mann et al. |
| 7,025,744 | B2 | 4/2006 | Utterberg et al. |
| 7,027,848 | B2 | 4/2006 | Robinson et al. |
| 7,043,288 | B2 | 5/2006 | Davis, III et al. |
| 7,060,059 | B2 | 6/2006 | Keith et al. |
| 7,061,593 | B2 | 6/2006 | Braig et al. |
| 7,096,124 | B2 | 8/2006 | Sterling et al. |
| 7,115,205 | B2 | 10/2006 | Robinson et al. |
| 7,128,727 | B2 | 10/2006 | Flaherty et al. |
| 7,139,593 | B2 | 11/2006 | Kavak et al. |
| 7,139,598 | B2 | 11/2006 | Hull et al. |
| 7,144,384 | B2 | 12/2006 | Gorman et al. |
| 7,171,252 | B1 | 1/2007 | Scarantino et al. |
| 7,190,988 | B2 | 3/2007 | Say et al. |
| 7,204,823 | B2 | 4/2007 | Estes et al. |
| 7,248,912 | B2 | 7/2007 | Gough et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 | 7/2008 | Ginsberg |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 | 2/2009 | Van Den Berghe et al. |
| 7,500,949 | B2 | 3/2009 | Gottlieb et al. |
| 7,509,156 | B2 | 3/2009 | Flanders |
| 7,547,281 | B2 | 6/2009 | Hayes et al. |
| 7,569,030 | B2 | 8/2009 | Lebel et al. |
| 7,608,042 | B2 | 10/2009 | Goldberger et al. |
| 7,651,845 | B2 | 1/2010 | Doyle, III et al. |
| 7,680,529 | B2 | 3/2010 | Kroll |
| 7,734,323 | B2 | 6/2010 | Blomquist et al. |
| 7,766,829 | B2 | 8/2010 | Sloan et al. |
| 7,785,258 | B2 | 8/2010 | Braig et al. |
| 7,806,854 | B2 | 10/2010 | Damiano et al. |
| 7,806,886 | B2 | 10/2010 | Kanderian, Jr. et al. |
| 7,918,825 | B2 | 4/2011 | OConnor et al. |
| 7,946,985 | B2 | 5/2011 | Mastrototaro et al. |
| 7,972,296 | B2 | 7/2011 | Braig et al. |
| 8,221,345 | B2 | 7/2012 | Blomquist |
| 8,251,907 | B2 | 8/2012 | Sterling et al. |
| 8,449,524 | B2 | 5/2013 | Braig et al. |
| 8,452,359 | B2 | 5/2013 | Rebec et al. |
| 8,454,576 | B2 | 6/2013 | Mastrototaro et al. |
| 8,467,980 | B2 | 6/2013 | Campbell et al. |
| 8,478,557 | B2 | 7/2013 | Hayter et al. |
| 8,547,239 | B2 | 10/2013 | Peatfield et al. |
| 8,597,274 | B2 | 12/2013 | Sloan et al. |
| 8,622,988 | B2 | 1/2014 | Hayter |
| 8,810,394 | B2 | 8/2014 | Kalpin |
| 9,061,097 | B2 | 6/2015 | Holt et al. |
| 9,171,343 | B1 | 10/2015 | Fischell et al. |
| 9,233,204 | B2 | 1/2016 | Booth et al. |
| 9,486,571 | B2 | 11/2016 | Rosinko |
| 9,579,456 | B2 | 2/2017 | Budiman et al. |
| 9,743,224 | B2 | 8/2017 | San Vicente et al. |
| 9,907,515 | B2 | 3/2018 | Doyle, III et al. |
| 9,980,140 | B1 | 5/2018 | Spencer et al. |
| 9,984,773 | B2 | 5/2018 | Gondhalekar et al. |
| 10,248,839 | B2 | 4/2019 | Levy et al. |
| 10,335,464 | B1 | 7/2019 | Michelich et al. |
| 10,583,250 | B2 | 3/2020 | Mazlish et al. |
| 10,737,024 | B2 | 8/2020 | Schmid |

(56) References Cited

U.S. PATENT DOCUMENTS

| | | | |
|---|---|---|---|
| 10,987,468 | B2 | 4/2021 | Mazlish et al. |
| 11,197,964 | B2 | 12/2021 | Sjolund et al. |
| 11,260,169 | B2 | 3/2022 | Estes |
| 2001/0021803 | A1 | 9/2001 | Blank et al. |
| 2001/0034023 | A1 | 10/2001 | Stanton, Jr. et al. |
| 2001/0034502 | A1 | 10/2001 | Moberg et al. |
| 2001/0051377 | A1 | 12/2001 | Hammer et al. |
| 2001/0053895 | A1 | 12/2001 | Vaillancourt |
| 2002/0010401 | A1 | 1/2002 | Bushmakin et al. |
| 2002/0010423 | A1 | 1/2002 | Gross et al. |
| 2002/0016568 | A1 | 2/2002 | Lebel et al. |
| 2002/0040208 | A1 | 4/2002 | Flaherty et al. |
| 2002/0123740 | A1 | 9/2002 | Flaherty et al. |
| 2002/0128543 | A1 | 9/2002 | Leonhardt |
| 2002/0147423 | A1 | 10/2002 | Burbank et al. |
| 2002/0155425 | A1 | 10/2002 | Han et al. |
| 2002/0161288 | A1* | 10/2002 | Shin ................... A61B 5/14865 |
| | | | 600/347 |
| 2003/0023148 | A1 | 1/2003 | Lorenz et al. |
| 2003/0050621 | A1 | 3/2003 | Lebel et al. |
| 2003/0060692 | A1 | 3/2003 | L. Ruchti et al. |
| 2003/0086074 | A1 | 5/2003 | Braig et al. |
| 2003/0086075 | A1 | 5/2003 | Braig et al. |
| 2003/0090649 | A1 | 5/2003 | Sterling et al. |
| 2003/0100040 | A1 | 5/2003 | Bonnecaze et al. |
| 2003/0130616 | A1 | 7/2003 | Steil et al. |
| 2003/0135388 | A1 | 7/2003 | Martucci et al. |
| 2003/0144582 | A1 | 7/2003 | Cohen et al. |
| 2003/0163097 | A1 | 8/2003 | Fleury et al. |
| 2003/0195404 | A1 | 10/2003 | Knobbe et al. |
| 2003/0208113 | A1 | 11/2003 | Mault et al. |
| 2003/0208154 | A1 | 11/2003 | Close et al. |
| 2003/0212379 | A1 | 11/2003 | Bylund et al. |
| 2003/0216627 | A1 | 11/2003 | Lorenz et al. |
| 2003/0220605 | A1 | 11/2003 | Bowman, Jr. et al. |
| 2004/0010207 | A1 | 1/2004 | Flaherty et al. |
| 2004/0034295 | A1 | 2/2004 | Salganicoff |
| 2004/0045879 | A1 | 3/2004 | Shults et al. |
| 2004/0051368 | A1 | 3/2004 | Caputo et al. |
| 2004/0064259 | A1 | 4/2004 | Haaland et al. |
| 2004/0097796 | A1 | 5/2004 | Berman et al. |
| 2004/0116847 | A1 | 6/2004 | Wall |
| 2004/0122353 | A1 | 6/2004 | Shahmirian et al. |
| 2004/0133166 | A1 | 7/2004 | Moberg et al. |
| 2004/0147034 | A1 | 7/2004 | Gore et al. |
| 2004/0171983 | A1 | 9/2004 | Sparks et al. |
| 2004/0203357 | A1 | 10/2004 | Nassimi |
| 2004/0204868 | A1 | 10/2004 | Maynard et al. |
| 2004/0215492 | A1 | 10/2004 | Choi |
| 2004/0220517 | A1 | 11/2004 | Starkweather et al. |
| 2004/0241736 | A1 | 12/2004 | Hendee et al. |
| 2004/0249308 | A1 | 12/2004 | Forssell |
| 2005/0003470 | A1 | 1/2005 | Nelson et al. |
| 2005/0020980 | A1 | 1/2005 | Inoue et al. |
| 2005/0022274 | A1 | 1/2005 | Campbell et al. |
| 2005/0033148 | A1 | 2/2005 | Haueter et al. |
| 2005/0049179 | A1 | 3/2005 | Davidson et al. |
| 2005/0065464 | A1 | 3/2005 | Talbot et al. |
| 2005/0065465 | A1 | 3/2005 | Lebel et al. |
| 2005/0075624 | A1 | 4/2005 | Miesel |
| 2005/0105095 | A1 | 5/2005 | Pesach et al. |
| 2005/0137573 | A1 | 6/2005 | Mclaughlin |
| 2005/0171503 | A1 | 8/2005 | Van Den Berghe et al. |
| 2005/0182306 | A1 | 8/2005 | Sloan |
| 2005/0192494 | A1 | 9/2005 | Ginsberg |
| 2005/0192557 | A1 | 9/2005 | Brauker et al. |
| 2005/0197621 | A1 | 9/2005 | Poulsen et al. |
| 2005/0203360 | A1* | 9/2005 | Brauker ............... A61B 5/7275 |
| | | | 600/345 |
| 2005/0203461 | A1 | 9/2005 | Flaherty et al. |
| 2005/0238507 | A1 | 10/2005 | Dilanni et al. |
| 2005/0261660 | A1 | 11/2005 | Choi |
| 2005/0272640 | A1 | 12/2005 | Doyle, III et al. |
| 2005/0277912 | A1 | 12/2005 | John |
| 2006/0009727 | A1 | 1/2006 | OMahony et al. |
| 2006/0079809 | A1 | 4/2006 | Goldberger et al. |
| 2006/0100494 | A1 | 5/2006 | Kroll |
| 2006/0134323 | A1 | 6/2006 | OBrien |
| 2006/0167350 | A1 | 7/2006 | Monfre et al. |
| 2006/0173406 | A1 | 8/2006 | Hayes et al. |
| 2006/0189925 | A1 | 8/2006 | Gable et al. |
| 2006/0189926 | A1 | 8/2006 | Hall et al. |
| 2006/0197015 | A1 | 9/2006 | Sterling et al. |
| 2006/0200070 | A1 | 9/2006 | Callicoat et al. |
| 2006/0204535 | A1 | 9/2006 | Johnson |
| 2006/0229531 | A1 | 10/2006 | Goldberger et al. |
| 2006/0253085 | A1 | 11/2006 | Geismar et al. |
| 2006/0264895 | A1 | 11/2006 | Flanders |
| 2006/0270983 | A1 | 11/2006 | Lord et al. |
| 2006/0276771 | A1 | 12/2006 | Galley et al. |
| 2006/0282290 | A1 | 12/2006 | Flaherty et al. |
| 2007/0016127 | A1 | 1/2007 | Staib et al. |
| 2007/0060796 | A1 | 3/2007 | Kim |
| 2007/0060869 | A1 | 3/2007 | Tolle et al. |
| 2007/0060872 | A1 | 3/2007 | Hall et al. |
| 2007/0083160 | A1 | 4/2007 | Hall et al. |
| 2007/0106135 | A1 | 5/2007 | Sloan et al. |
| 2007/0116601 | A1 | 5/2007 | Patton |
| 2007/0118405 | A1 | 5/2007 | Campbell et al. |
| 2007/0129690 | A1 | 6/2007 | Rosenblatt et al. |
| 2007/0142720 | A1 | 6/2007 | Ridder et al. |
| 2007/0173761 | A1 | 7/2007 | Kanderian et al. |
| 2007/0173974 | A1 | 7/2007 | Lin et al. |
| 2007/0179352 | A1 | 8/2007 | Randlov et al. |
| 2007/0191716 | A1 | 8/2007 | Goldberger et al. |
| 2007/0197163 | A1 | 8/2007 | Robertson |
| 2007/0225675 | A1 | 9/2007 | Robinson et al. |
| 2007/0244381 | A1 | 10/2007 | Robinson et al. |
| 2007/0249007 | A1 | 10/2007 | Rosero |
| 2007/0264707 | A1 | 11/2007 | Liederman et al. |
| 2007/0282269 | A1 | 12/2007 | Carter et al. |
| 2007/0287985 | A1 | 12/2007 | Estes et al. |
| 2007/0293843 | A1 | 12/2007 | Ireland et al. |
| 2008/0033272 | A1 | 2/2008 | Gough et al. |
| 2008/0051764 | A1 | 2/2008 | Dent et al. |
| 2008/0058625 | A1 | 3/2008 | McGarraugh et al. |
| 2008/0065050 | A1 | 3/2008 | Sparks et al. |
| 2008/0071157 | A1 | 3/2008 | McGarraugh et al. |
| 2008/0071158 | A1 | 3/2008 | McGarraugh et al. |
| 2008/0078400 | A1 | 4/2008 | Martens et al. |
| 2008/0097289 | A1 | 4/2008 | Steil et al. |
| 2008/0132880 | A1 | 6/2008 | Buchman |
| 2008/0161664 | A1 | 7/2008 | Mastrototaro et al. |
| 2008/0172026 | A1 | 7/2008 | Blomquist |
| 2008/0177165 | A1 | 7/2008 | Blomquist et al. |
| 2008/0188796 | A1 | 8/2008 | Steil et al. |
| 2008/0200838 | A1 | 8/2008 | Goldberger et al. |
| 2008/0206067 | A1 | 8/2008 | De Corral et al. |
| 2008/0208113 | A1 | 8/2008 | Damiano et al. |
| 2008/0214919 | A1 | 9/2008 | Harmon et al. |
| 2008/0228056 | A1 | 9/2008 | Blomquist et al. |
| 2008/0249386 | A1 | 10/2008 | Besterman et al. |
| 2008/0269585 | A1 | 10/2008 | Ginsberg |
| 2008/0269714 | A1 | 10/2008 | Mastrototaro et al. |
| 2008/0269723 | A1 | 10/2008 | Mastrototaro et al. |
| 2008/0287906 | A1 | 11/2008 | Burkholz et al. |
| 2009/0006061 | A1 | 1/2009 | Thukral et al. |
| 2009/0018406 | A1 | 1/2009 | Yodfat et al. |
| 2009/0030398 | A1 | 1/2009 | Yodfat et al. |
| 2009/0036753 | A1 | 2/2009 | King |
| 2009/0043240 | A1 | 2/2009 | Robinson et al. |
| 2009/0054753 | A1 | 2/2009 | Robinson et al. |
| 2009/0069743 | A1 | 3/2009 | Krishnamoorthy et al. |
| 2009/0069745 | A1 | 3/2009 | Estes et al. |
| 2009/0069787 | A1 | 3/2009 | Estes et al. |
| 2009/0099521 | A1 | 4/2009 | Gravesen et al. |
| 2009/0105573 | A1 | 4/2009 | Malecha |
| 2009/0131861 | A1 | 5/2009 | Braig et al. |
| 2009/0156922 | A1 | 6/2009 | Goldberger et al. |
| 2009/0156924 | A1 | 6/2009 | Shariati et al. |
| 2009/0163781 | A1 | 6/2009 | Say et al. |
| 2009/0192745 | A1* | 7/2009 | Kamath ............. A61B 5/14532 |
| | | | 702/85 |
| 2009/0198350 | A1 | 8/2009 | Thiele |

(56) References Cited

U.S. PATENT DOCUMENTS

| | | |
|---|---|---|
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0179409 A1* | 7/2010 | Kamath ................ A61B 5/725 |
| | | 702/19 |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birthwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0279335 A1* | 9/2016 | Sjöstedt .................. A61M 5/24 |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1* | 8/2019 | Palerm ................ A61B 5/4839 |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0189603 A1 | 6/2022 | Damiano et al. |

(56) References Cited

U.S. PATENT DOCUMENTS

FOREIGN PATENT DOCUMENTS

| CA | 3046100 | A1 * | 6/2018 | ......... A61B 5/14532 |
| CA | 3055770 | A1 * | 9/2018 | ........... A61B 5/0004 |
| CN | 1297140 | A | 5/2001 | |
| DE | 19756872 | A1 | 7/1999 | |
| EP | 0341049 | A2 | 11/1989 | |
| EP | 0496305 | A2 | 7/1992 | |
| EP | 0549341 | A1 | 6/1993 | |
| EP | 1491144 | A1 | 12/2004 | |
| EP | 0801578 | B1 | 7/2006 | |
| EP | 2139382 | A1 | 1/2010 | |
| EP | 2397181 | A1 | 12/2011 | |
| EP | 2666520 | A1 | 11/2013 | |
| EP | 2695573 | A2 | 2/2014 | |
| EP | 2830499 | A1 | 2/2015 | |
| EP | 2943149 | A1 | 11/2015 | |
| EP | 3177344 | A1 | 6/2017 | |
| EP | 3314548 | A1 | 5/2018 | |
| EP | 1571582 | B1 | 4/2019 | |
| EP | 2897071 | B1 | 5/2019 | |
| EP | 3607985 | A1 | 2/2020 | |
| GB | 2443261 | A | 4/2008 | |
| JP | 51125993 | A | 11/1976 | |
| JP | 02131777 | A | 5/1990 | |
| JP | 2004283378 | A | 10/2007 | |
| JP | 2017525451 | A | 9/2017 | |
| JP | 2018153569 | A | 10/2018 | |
| JP | 2019525276 | A | 9/2019 | |
| TW | 200740148 | A | 10/2007 | |
| TW | M452390 | U | 5/2013 | |
| WO | 9800193 | A1 | 1/1998 | |
| WO | 9956803 | A1 | 11/1999 | |
| WO | 0030705 | A1 | 6/2000 | |
| WO | 200032258 | A1 | 6/2000 | |
| WO | 0172354 | A2 | 10/2001 | |
| WO | 2002015954 | A1 | 2/2002 | |
| WO | 2002043866 | A2 | 6/2002 | |
| WO | 2002082990 | A1 | 10/2002 | |
| WO | 2003016882 | A1 | 2/2003 | |
| WO | 2003039362 | A1 | 5/2003 | |
| WO | 2003045233 | A1 | 6/2003 | |
| WO | 2004043250 | A1 | 5/2004 | |
| WO | 2005110601 | A1 | 5/2004 | |
| WO | 2004092715 | A1 | 10/2004 | |
| WO | WO-2005051170 | A2 * | 6/2005 | ............ A61B 5/076 |
| WO | 2005082436 | A1 | 9/2005 | |
| WO | 2005113036 | A1 | 12/2005 | |
| WO | 2006053007 | A2 | 5/2006 | |
| WO | 2007064835 | A2 | 6/2007 | |
| WO | 2007078937 | A1 | 7/2007 | |
| WO | 2008024810 | A2 | 2/2008 | |
| WO | 2008029403 | A1 | 3/2008 | |
| WO | 2008133702 | A1 | 11/2008 | |
| WO | 2009045462 | A1 | 4/2009 | |
| WO | 2009049252 | A1 | 4/2009 | |
| WO | 2009066287 | A3 | 5/2009 | |
| WO | 2009066288 | A1 | 5/2009 | |
| WO | 2009098648 | A2 | 8/2009 | |
| WO | 2009134380 | A2 | 11/2009 | |
| WO | 2010053702 | A1 | 5/2010 | |
| WO | 2010132077 | A1 | 11/2010 | |
| WO | 2010138848 | A1 | 12/2010 | |
| WO | 2010147659 | A2 | 12/2010 | |
| WO | 2011095483 | A1 | 8/2011 | |
| WO | 2012045667 | A2 | 4/2012 | |
| WO | 2012108959 | A1 | 8/2012 | |
| WO | 2012134588 | A1 | 10/2012 | |
| WO | 2012177353 | A1 | 12/2012 | |
| WO | 2012178134 | A2 | 12/2012 | |
| WO | 2013078200 | A1 | 5/2013 | |
| WO | 2013134486 | A2 | 9/2013 | |
| WO | 20130149186 | A1 | 10/2013 | |
| WO | 2013177565 | A1 | 11/2013 | |
| WO | 2013182321 | A1 | 12/2013 | |
| WO | 2014109898 | A1 | 7/2014 | |
| WO | 2014110538 | A1 | 7/2014 | |
| WO | 2014194183 | A2 | 12/2014 | |
| WO | 2015056259 | A1 | 4/2015 | |
| WO | 2015061493 | A1 | 4/2015 | |
| WO | 2015073211 | A1 | 5/2015 | |
| WO | 2015081337 | A2 | 6/2015 | |
| WO | 2015187366 | A1 | 12/2015 | |
| WO | 2016004088 | A1 | 1/2016 | |
| WO | 2016022650 | A1 | 2/2016 | |
| WO | 2016041873 | A1 | 3/2016 | |
| WO | 2016089702 | A1 | 6/2016 | |
| WO | 2016141082 | A1 | 9/2016 | |
| WO | 2016161254 | A1 | 10/2016 | |
| WO | 2017004278 | A1 | 1/2017 | |
| WO | 2017091624 | A1 | 6/2017 | |
| WO | 2017105600 | A1 | 6/2017 | |
| WO | 2017184988 | A1 | 10/2017 | |
| WO | 2017205816 | A1 | 11/2017 | |
| WO | 2018009614 | A1 | 1/2018 | |
| WO | 2018067748 | A1 | 4/2018 | |
| WO | 2018120104 | A1 | 7/2018 | |
| WO | 2018136799 | A1 | 7/2018 | |
| WO | 2018204568 | A1 | 11/2018 | |
| WO | 2019077482 | A1 | 4/2019 | |
| WO | 2019094440 | A1 | 5/2019 | |
| WO | 2019213493 | A1 | 11/2019 | |
| WO | 2019246381 | A1 | 12/2019 | |
| WO | 2020081393 | A1 | 4/2020 | |
| WO | 2021011738 | A1 | 1/2021 | |

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

(56)         References Cited

OTHER PUBLICATIONS

"Read NFC Tags with an iPHone App on iOS 11", GoToTags, Sep. 11, 2017, web <https://gototags.com/blog/read-hfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

(56)             References Cited

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010 (OPTIS. 247VPC).

International Search Report and Written Opinion in PCT/US2008/079641 (Optis.203VPC) dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech, vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

(56)            References Cited

OTHER PUBLICATIONS

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

100

DEVICES AND METHODS FOR INITIALIZATION OF DRUG DELIVERY DEVICES USING MEASURED ANALYTE SENSOR INFORMATION

RELATED APPLICATIONS

This application claims the benefit of U.S. Provisional Patent Application No. 63/180,777, filed Apr. 28, 2021, the contents of which are incorporated herein by reference in their entirety.

BACKGROUND

Automated drug delivery systems may use measured patient analyte values to determine drug dosages. For example, an automated insulin delivery system may rely on correct blood glucose readings from blood glucose monitors associated with the patient. The measured analyte readings may be used to calculate a dosage of the drug based on the analyte values and/or predicted trend lines based on the analyte values. In this manner, an automated drug delivery system may operate to provide an accurate and efficient level of the drug that is personalized for the patient and their specific physiological condition at the time of the drug delivery cycle.

If the automated drug delivery system is not able to receive patient analyte values (or a sufficient number of analyte values to make a determination), the system may rely on fallback mechanisms for calculating drug dosage during a delivery cycle, such as using conservative or default drug dosages or even stopping drug delivery. The fallback mechanisms are typically configured to provide a safe level of the drug; however, they reduce the overall efficacy of the automated drug delivery system because they are not able to provide a dose that relates directly to a current physiological condition (for instance, analyte levels associated with the drug) of the patient.

Accordingly, automated drug delivery devices may benefit from processes that are able to accurately and safely administer drug dosages specialized for the patient in the absence of analyte measurements.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with various embodiments of the present disclosure is a drug delivery device, having a processor a memory storing instructions. The instructions, when executed by the processor, may operate the drug delivery device to receive a present analyte measurement value from an analyte sensor during an initialization of the drug delivery device, receive at least one backfill value measured by the analyte sensor prior to the initialization, calculate a dosage of a drug using the present analyte measurement value and the at least one backfill value, and deliver the dosage of the drug.

In some embodiments of the drug delivery device, the at least one backfill value may include a plurality of analyte values determined by the analyte sensor prior to the initialization of the drug delivery device. In various embodiments of the drug delivery device, the at least one backfill value may include a plurality of analyte values stored by an external controller prior to the initialization of the drug delivery device.

In some embodiments of the drug delivery device, the instructions, when executed by the processor, may operate the drug delivery device to determine an analyte concentration trend based on the present analyte measurement and the at least one backfill value. In exemplary embodiments of the drug delivery device, the instructions, when executed by the processor, may operate the drug delivery device to calculate the dosage based on the analyte concentration trend. In various embodiments of the drug delivery device, the instructions, when executed by the processor, may operate the drug delivery device to receive the at least one backfill value from a controller located external to the drug delivery device.

In some embodiments of the drug delivery device, the initialization is associated with an exchange of the drug delivery device for a deactivated drug delivery device.

In various embodiments of the drug delivery device, the instructions, when executed by the processor, may operate the drug delivery device to determine whether the at least one backfill value meets a safety constraint. In some embodiments of the drug delivery device, the safety constraint may include a minimum number of values in the at least one backfill value. In exemplary embodiments of the drug delivery device, the safety constraint may include the at least one backfill value being within a correlation threshold of the present analyte measurement value.

In some embodiments of the drug delivery device, the analyte measurement value is a blood glucose measurement value, and the drug is insulin, glucagon, a glucagon-like peptide or a combination of at least two of insulin, glucagon or the glucagon-like peptide.

In accordance with various embodiments of the present disclosure is a controller for a drug delivery device, having a processor and a memory storing instructions. The instructions, when executed by the processor, may operate the controller to receive a deactivation indication from a first drug delivery device that the first drug delivery device is being deactivated, establish a connection to a sensor device responsive to the deactivation indication, and collect sensor measurement values from the sensor device as backfill values.

In some embodiments of the controller, the instructions, when executed by the processor, may operate the controller to receive an initialization indication from a second drug delivery device that the second drug delivery device is being initialized, and provide the at least one backfill value to the second drug delivery device.

In some embodiments of the controller, the initialization is associated with an exchange of the second drug delivery device for the first drug delivery device. In various embodiments of the controller, the analyte measurement value is a blood glucose measurement value, and the drug is insulin, glucagon, a glucagon-like peptide or a combination of at least two of insulin, glucagon or the glucagon-like peptide.

In accordance with various embodiments of the present disclosure is a computer-implemented method of operating a drug delivery device. The method may include, via a processor of the drug delivery device, receiving a present analyte measurement value from an analyte sensor during an initialization of the drug delivery device, receiving at least one backfill value measured by the analyte sensor prior to the initialization, calculating a dosage of a drug using the present analyte measurement value and the at least one backfill value, and delivering the dosage of the drug.

In some embodiments of the method, the at least one backfill value may include a plurality of analyte values determined by the analyte sensor prior to the initialization of the drug delivery device. In some embodiments of the method, the at least one backfill value may include a plurality of analyte values stored by an external controller prior to the initialization of the drug delivery device.

In some embodiments of the method, the method may include determining an analyte concentration trend based on the present analyte measurement and the at least one backfill value. In some embodiments of the method, the method may include calculating the dosage based on the analyte concentration trend.

In some embodiments of the method, the method may include receiving the at least one backfill value from a controller located external to the drug delivery device.

In some embodiments of the method, the initialization is associated with an exchange of the drug delivery device for a deactivated drug delivery device.

In some embodiments of the method, the method may include determining whether the at least one backfill value meets a safety constraint. In some embodiments of the method, the safety constraint may include a minimum number of values in the at least one backfill value. In some embodiments of the method, the safety constraint may include the at least one backfill value being within a correlation threshold of the present analyte measurement value.

In some embodiments of the method, the analyte measurement value is a blood glucose measurement value, and the drug is insulin, glucagon, a glucagon-like peptide or a combination of at least two of insulin, glucagon or the glucagon-like peptide.

In accordance with various embodiments of the present disclosure is a computer-implemented method of operating a controller for a drug delivery device, comprising, via a processor of the controller, receiving a deactivation indication from a first drug delivery device that the first drug delivery device is being deactivated, establishing a connection to a sensor device responsive to the deactivation indication; and collecting sensor measurement values from the sensor device as backfill values.

In some embodiments of the method, the method may include receiving an initialization indication from a second drug delivery device that the second drug delivery device is being initialized, and providing the at least one backfill value to the second drug delivery device. In various embodiments of the method, the initialization is associated with an exchange of the second drug delivery device for the first drug delivery device.

In some embodiments of the method, the analyte measurement value is a blood glucose measurement value, and the drug is insulin, glucagon, a glucagon-like peptide or a combination of at least two of insulin, glucagon or the glucagon-like peptide.

Figure 1:
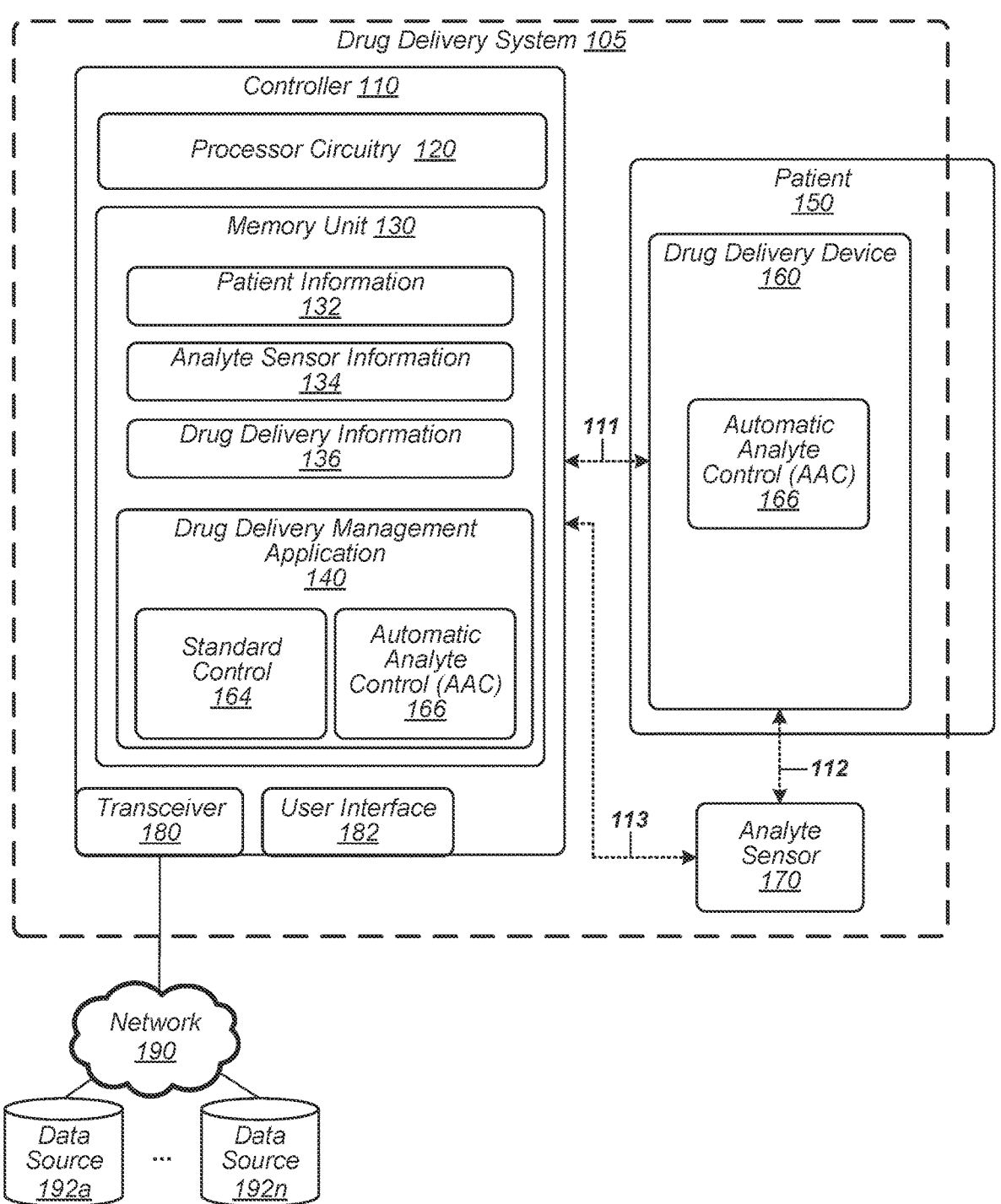
FIG. 1 illustrates a first exemplary embodiment of an operating environment in accordance with the present disclosure.

The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements.

DETAILED DESCRIPTION

As described below, a drug delivery system may include a number of components, such as a drug delivery device, a controller, and an analyte sensor. The drug delivery device may be controlled and operate based on signals containing information received from the analyte sensor. Control may be based on an application executing on the drug delivery device, the controller, or the analyte sensor, or the application may be distributed between two or more of the drug delivery device, the controller, or the analyte sensor. For example, the drug delivery device may be configured to deliver a drug at a dosage or frequency based on a measured analyte concentration associated with a patient.

An example of an automatic analyte control application or logic circuit may be specific to a particular type of analyte. Non-limiting examples of analytes may include blood glucose, a hormone, a protein, a medication, ketone, alcohol level, a concentration of the drug itself (e.g., insulin), and the like. A control application specific to controlling a patient's blood glucose may be an Automatic Glucose Control (AGC) application that may rely on a blood glucose measurement value and other information that may be provided by a continuous glucose monitor (CGM). "Automatic glucose control" may refer to an algorithm or computer application that is operable to use blood glucose measurements to determine amounts of a drug to be delivered to a user to in order to maintain the user's measured blood glucose within a set range of blood glucose measurement values. "Blood glucose measurement value" may refer to a numerical value representative of an amount of glucose in a user's blood that has the units of milligrams per deciliter (mg/dL). The other information provided by the CGM may be included as part of, or separately from, the blood glucose measurement value. The AGC may be operable to estimate and store the estimated values of CGM based upon various parameters within the drug delivery system. Such future trend information may be useful in case of missing CGM values to estimate suggested insulin for a short duration.

Although insulin delivery devices, insulin, blood glucose, AGC applications, and CGM devices are used in examples in the present disclosure, embodiments are not so limited as these are provided for illustrative purposes. Embodiments may operate with various types of fluid or drug delivery devices, drugs or other fluids, analytes, automated drug delivery applications, and/or analyte sensors in accordance with the teachings of the present disclosure.

A drug delivery system may include a component that requires replacement based on a time interval, delivery of a volume of the drug, and/or the like. For example, a wearable insulin delivery device may include an insulin pump unit that may include, among other things, a pump, an insulin reservoir, and control elements to control the pump to deliver a dosage of insulin from the insulin reservoir. The insulin pump unit, or a portion thereof, such as the drug or a reservoir containing the drug, may require replacement every 48 to 72 hours or after delivery of a certain volume of insulin (for instance, 200 units). The insulin pump unit may be controlled by an AGC operating on the insulin pump unit and/or an external logic device, such as a computing device (for instance, a smart phone) or a dedicated personal diabetes manager (PDM) device (see, for example, FIGS. 1 and 5). The AGC may determine insulin dosages based on blood glucose values measured by a CGM. A non-limiting example of an insulin pump unit may include a "Pod" component of an OmniPod® device or system provided by Insulet Corporation of Acton, Massachusetts, United States, for example, as described in U.S. Pat. Nos. 7,303,549; 7,137,964; and/or 6,740,059, each of which is incorporated herein by reference in its entirety.

Deactivation and removal of the previous or old insulin pump unit and installation and activation of the new insulin pump unit may require a substantive amount of time, such as about 5 minutes to about 25 minutes. Depending on the efficiency of the patient and associated drug delivery device components, this may take much longer. In a conventional insulin delivery device, CGM values may not be available or may not be available to the insulin delivery system in a form capable of being used to determine insulin dosage by the AGC until the new insulin pump unit has gone through an initialization or "warm up" period. If the insulin pump unit requires changing every 72 hours, this may lead to a significant amount of time on a weekly basis where CGM-based insulin dosage control is not available to the patient. In the absence of CGM-based insulin dosage control, insulin delivery may be based on conservative default values, such as a patient's basal dosage or less, which may not adequately control a patient's dynamic blood glucose level. In addition, patient conditions (such as a diabetes patient being in a hypo- or hyper-glycemic state) may not be transferred to the new insulin pump unit.

Figure 3:
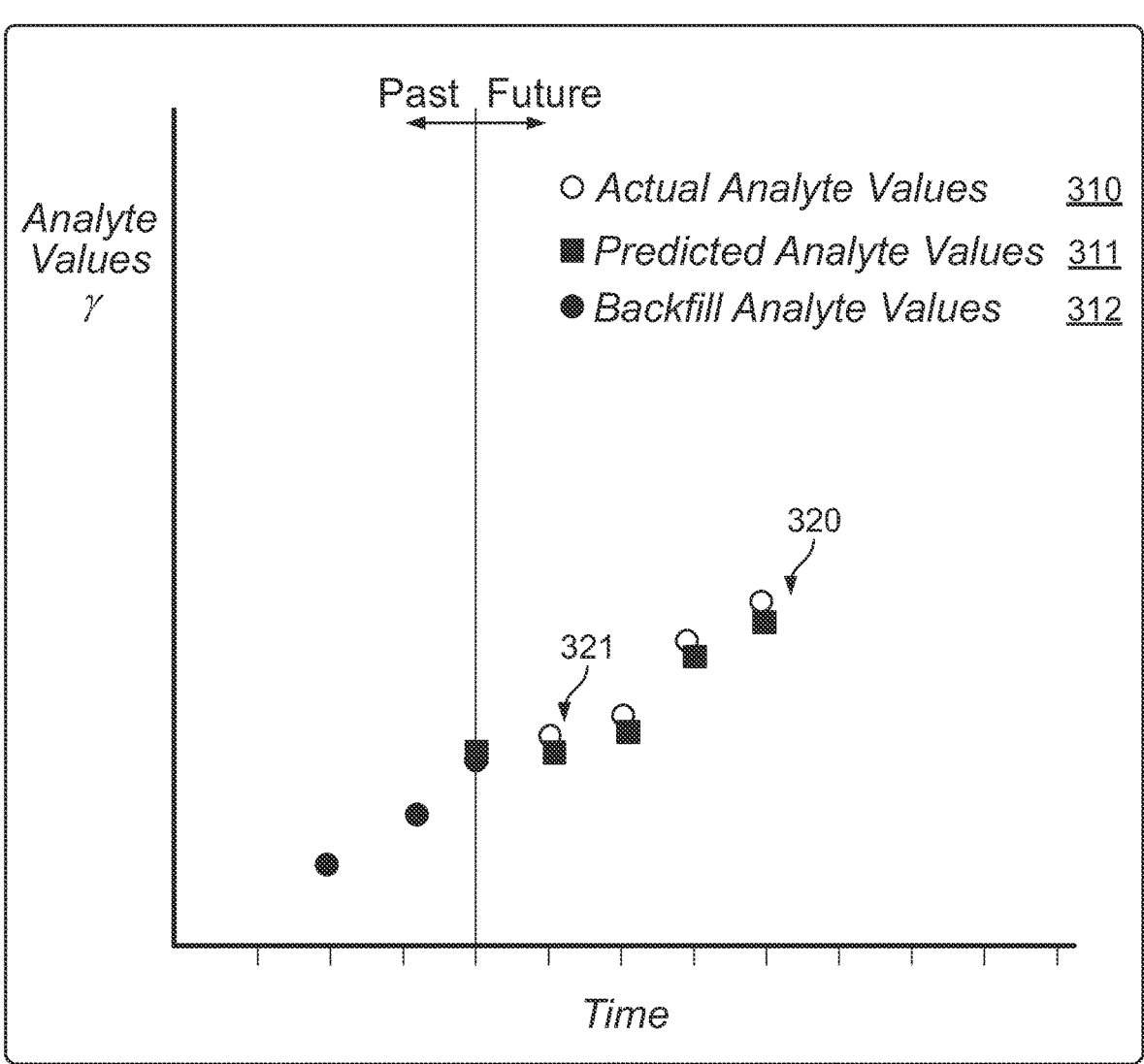
FIG. 3 illustrates a graph of backfill, actual, and predicted analyte values in accordance with the present disclosure.

For example, during initialization, AGC systems typically assume that the initial input CGM value has been maintained at a constant value, and establishes a predicted glucose trend as a flat trajectory with the first input CGM value received during initialization (see, for example, FIG. 3). As this is not the user's true CGM trend, it is not safe to deliver insulin based on this trajectory immediately, and the system typically delivers a conservative value (for instance, basal or another default, predetermined value).

Accordingly, systems and methods according to some embodiments, may provide processes and a drug delivery device capable of measurement-based drug delivery during the initialization (or "warm up") period. For example, during activation or initialization of the device (for instance, an insulin pump unit), the controller may send CGM values, trends, and/or a few previous CGM values before and/or during device activation. This is during the time window when the previous device was deactivated but the new device was not yet activated. In this opportunistic window, the controller can continue to receive the CGM value by connecting over its own communication path with the CGM and may send this information immediately after activation. In addition, patient conditions under the old insulin pump unit may be immediately or substantially immediately transferred to the new insulin pump unit. Accordingly, a new insulin pump unit may operate to provide insulin based on control processes associated with the patient conditions, such as a hypo- or hyper-glycemic state.

Accordingly, some embodiments may provide methods that manage (or essentially eliminate) the initial blanking period of conventional device where the drug delivery algorithm call is delayed and/or is active but provides conservative dosage values (without the use of CGM data) for a time period and/or during warmup cycles. The AGC process can immediately determine trajectory and time lapse between previous activation and the current activation, thereby approximating the insulin needed immediately and allowing for completion of the warmup process sooner or immediately, depending upon the recent information and the completeness of the CGM information, trend, and past values during the activation. For example, in some embodiments, a new insulin pump unit may be activated immediately or substantially immediately (for instance, within a time period substantially smaller than for conventional devices, such as within the first 1 to 5 minutes of installation on the patient) because the AGC algorithm may use the previous CGM values, trend, and most recent information to accelerate the warm-up to exit out of conservative mode and start CGM-based insulin delivery.

Therefore, drug delivery systems and methods for operating drug delivery devices according to some embodiments may provide multiple technological advantages over conventional systems and methods. In one non-limiting technological advantage, systems may be configured to provide analyte-based drug delivery control during initialization (or "warm up") of a new device. Conventional devices were only capable of proceeding with a conservative drug delivery approach during and for a certain period after activation of a new drug delivery device. The non-limiting technological advantages may include improvements in computing technology and/or technical field. For instance, systems and methods according to some embodiments may improve conventional logic devices, controllers, computing devices, and/or other computing technology for controlling drug delivery systems by providing computing technology capable of analyte-based drug delivery control during an initialization process of a drug delivery device. In addition, systems and methods according to some embodiments may improve the field of automated drug delivery, including, for example, wearable insulin drug delivery devices and associated processes for controlling these devices, drug therapy, diabetes therapy, and/or the like. Furthermore, the methods according to some embodiments may be applied to the practical applications of controlling a drug delivery device, providing a dosage of a drug to a patient, drug therapy, and/or diabetes therapy. Embodiments are not limited in this context. Additional technological advantages, practical applications, and improvements to computing technology and/or technical fields would be known to a person of skill in the art in view of the teachings of the present disclosure.

FIG. 1 illustrates features of the subject matter in accordance with an embodiment of a drug delivery system 105 of an operating environment 100. "Drug delivery system" may refer to a drug delivery device and an analyte sensor, such as a continuous glucose monitor (CGM), and, in some configurations, a controller. "Drug delivery device" may refer to a device configured to administer a liquid drug to a user. A drug delivery device may be the same or substantially similar to the OmniPod® referenced in the present disclosure. The drug delivery device may respond to command signals received from a controller, which may be a separate device. Alternatively, the drug delivery device may be configured with a controller including a processor and memory that is not separate from the drug delivery device but is operable to perform functions like or in lieu of a separate controller. "Controller" may refer to a device having a processor that is configured to control operation of a drug delivery device and transmit and receive information related to measured blood glucose of a user associated with the drug delivery device and the controller. The functions performed by the controller may be executed by a processor integral to the drug delivery device. "Continuous glucose monitor" may refer to a wearable device that may at least include a sensor configured to measure blood glucose of a wearer, a transmitter to transmit blood glucose measurement values measured by the sensor, and logic circuitry that controls the sensor and the transmitter.

Drug delivery system 105 may include a logic device or controller 110, drug delivery device 160 and an analyte sensor 170. Controller 110 may communicate with the drug delivery device 160 via communication link 111 and the drug delivery device 160 may communicate with the analyte sensor 170 via a communication link 112. "Communication link" may refer to a signal pathway between a first device and a second device. As described below, information may be exchanged between the first device and the second device where both devices may transmit and receive information or other signals.

In some embodiments, controller 110 may be a smart phone, PDM, or other mobile computing form factor in wired or wireless communication with drug delivery device 160. For example, controller device 110 and drug delivery device 160 may communicate via various wireless protocols, including, without limitation, Wi-Fi (i.e., IEEE 802.11), radio frequency (RF), Bluetooth®, Zigbee™, near field communication (NFC), Medical Implantable Communications Service (MICS), and/or the like. In another example, controller 110 and adjustment compliance device may communicate via various wired protocols, including, without limitation, universal serial bus (USB), Lightning, serial, and/or the like.

Although controller 110 (and components thereof), drug delivery device 160, and analyte sensor 170 are depicted as separate devices, embodiments are not so limited. For example, in some embodiments, controller 110, drug delivery device 160, and/or analyte sensor 170 may be a single device. In another example, some or all of the components of controller 110 may be included in drug delivery device 160. For example, drug delivery device 160 may include processor circuitry 120, memory unit 130, and/or the like. In some embodiments, each of controller 110 and drug delivery device 160 may include a separate processor circuitry 120, memory unit 130, and/or the like capable of facilitating automatic analyte control and/or device initialization processes according to some embodiments, either individually or in operative combination. Embodiments are not limited in this context (see, for example, FIG. 5)

Drug delivery device 160 may include a number of components to facilitate automated delivery of a drug to patient 150. For example, drug delivery device 160 may include a reservoir for storing the drug, a needle or cannula for delivering the drug into the body of the patient, and a pump for transferring the drug from the reservoir, through the needle or cannula, and into the body of the patient. In some embodiments, the drug may be or may include insulin. Drug delivery device 160 may also include a power source, such as a battery, for supplying power to the pump and/or other components of drug delivery device 160. Embodiments are not limited in this context, for example, as drug delivery device 160 may include more or fewer components.

"Analyte sensor" may refer to a sensing and measuring device that may be configured to measure one or more of lactate, ketones, uric acid, sodium, a protein, potassium, alcohol levels, hormone levels, blood glucose, a medication, a drug, a chemotherapy drug, glucagon or a glucagon-like peptide, and/or the like. In some examples, analyte sensor 170 may be configured as a continuous glucose monitor (CGM), which may refer to a wearable device that may at least include a sensor configured to measure blood glucose of a wearer, a transmitter to transmit blood glucose measurement values measured by the sensor (for example, to controller 110 and/or drug delivery device 160), and logic circuitry that controls the sensor and the transmitter. Analyte sensor 170 may be configured with a processor, a communication device, a memory, a sensing/measuring device, and/or other components (see, for example, FIG. 5). Analyte sensor 170 may output analyte measurement values to any devices that are communicatively coupled to analyte sensor 170 when operating properly (e.g., while there is full power supply, established wireless connectivity, proper operation of the sensing/measuring device, and whatever other functions enable the analyte sensor to detect and output an analyte measurement value).

In drug delivery system 105 of FIG. 1, analyte sensor 170 and drug delivery device 160 may be communicatively coupled to one another, and controller 110 and drug delivery device 160 may be communicatively coupled to one another. For example, controller 110 may be wirelessly coupled to drug delivery device 160 via communication link 111 and drug delivery device 160 may be wirelessly coupled to analyte sensor 170 via communication link 112. In some embodiments, controller 110 and analyte sensor 170 may be communicatively coupled to one another, for instance, via communications link 113.

Analyte sensor 170 may provide an analyte measurement value at a specific time during an operational time period to drug delivery device 160. "Analyte measurement value" may refer to a numerical value representative of an amount of an analyte being monitored by an analyte sensor and that has the units in common usage of the analyte being monitored, such as milligrams per deciliter (mg/dL), a percentage, or the like. In an example, analyte sensor 170 may be configured to output an analyte measurement value at a predetermined cadence (e.g., every 1, 2, 3, 5, or 10 minutes) or once within a set period of time (e.g., at time=0 in a 5-minute period of time). The set period of time in the example of a diabetes treatment plan may be referred to as a "cycle" or "cycle time," which may last 5 minutes, or about 5 minutes, about 3 minutes, or about 10 minutes, or the like. A specific time during the operation may be at the beginning of the operational time period.

The outputted analyte measurement value is intended, in this embodiment, for receipt by the drug delivery management application 140 executing on controller 110 and/or automatic analyte control (AAC) application executing on drug delivery device 160, but may be shared with other applications, such as an automatic medication delivery application, an artificial pancreas application, and/or the like. The analyte measurement values may include information that includes an analyte measurement value, such as a blood glucose measurement value, but also information such as analyte rate of change, status information related to a sensing/measuring device in analyte sensor 170, and/or the like.

Controller 110 may be configured with a processor or processor circuitry 120, a memory unit 130, a user interface 182, a communication device or transceiver 180, and/or the like. Memory unit 130 may store information, such as patient information 134, analyte sensor information 134, drug delivery information 136, each of which may include previous analyte measurement values, delivered drug dosages, and/or the like.

In some embodiments, patient information 132 may include information associated with patient 150, including, without limitation, demographic information, physical information (for instance, height, weight, and/or the like), diabetes condition information (for instance, type of diagnosed diabetes (T1D or T2D)), insulin needs (for instance, MDI information, TDI information, insulin types, basal dosage information, bolus dosage information, and/or the like), activity information (for instance, meals and/or meal times, carbohydrate intake, exercise information, and/or the like), insulin sensitivity information, IOB information, BG events (for example, hypoglycemic episodes or hyperglycemic episodes), and/or the like. In some embodiments, at least a portion of patient information 132 may be manually entered by patient 150 or a caregiver, for example, via a user interface of diabetes management application 140. In other embodiments, at least a portion of patient information 132 may be downloaded automatically from network 190 or cloud-based services 611, or transferred automatically from a prior drug delivery device 160 to a new drug delivery device 160. In some embodiments, patient information 132 may include historical information, such as historical values associated with mealtimes, carbohydrate intake, exercise times, and/or the like.

In some embodiments, analyte sensor information 134 may include information associated with analyte sensor 170, including analyte values measured by analyte sensor 170. For example, for a CGM sensor, analyte sensor information 134 may include blood glucose measurements of patient 150. In various embodiments, analyte sensor information 134 may include historical or "backfill" values. In some embodiments, values measured by analyte sensor 170 may be stored as backfill values. In various embodiments, backfill values may include a set number of previous values (for instance, from 2 to 50 previous values) or may include values measured during a previous time period (for instance, the previous 2 minutes to about 60 minutes or the previous 1 cycle to 10 cycles). In some embodiments, the historical or backfill values may be saved by analyte sensor 170, controller 110, and/or drug delivery device 160 and stored in various locations, including on analyte sensor 170, controller 110, drug delivery device 160, and/or a data source 192*a-n* (including a remote computing device) accessible via network 190.

In some embodiments, drug delivery information 136 may include information used to determine the dosage of the drug to deliver to patient 150, for instance, based on analyte sensor information 134. For example, AAC 166 may determine a dosage of the drug to be delivered based on an analyte value and/or trend determined based on analyte sensor information 134. For example, for an insulin delivery device, AAC 166 may determine a dosage of insulin to deliver for an upcoming delivery cycle based on a trend of patient blood glucose concentrations predicted based on blood glucose values measured by a CGM analyte sensor 170 in order to maintain a blood glucose concentration target or range.

Additionally, memory unit 130 may store computer applications, such as a drug delivery management application 140, which may be or may include a medication delivery application (MDA), an automatic analyte control application, an AGC application, an analyte-based drug delivery application, an automatic analyte control application, an artificial pancreas application, an automated insulin delivery (AID) application, and/or the like, that are executable by processor circuitry 120 and configure processor circuitry 120 to perform different functions according to some embodiments of the present disclosure. Drug delivery management application may include an "automatic analyte control application" that may refer to a computer application that is operable to execute an algorithm operable to use analyte measurement values, including blood glucose measurement values, to locally determine amounts of a drug to be delivered to a user.

Controller 110 when executing drug delivery management application 140 may be configured to set operational parameters for drug delivery device 160, such as user preferences for drug deliveries (e.g., times, durations, and amounts of basal and/or bolus deliveries) and notifications/alarms, drug delivery limits, user statistics (e.g., height, weight, gender, age, type of diabetes, or the like) as well as other settings.

Figure 5:
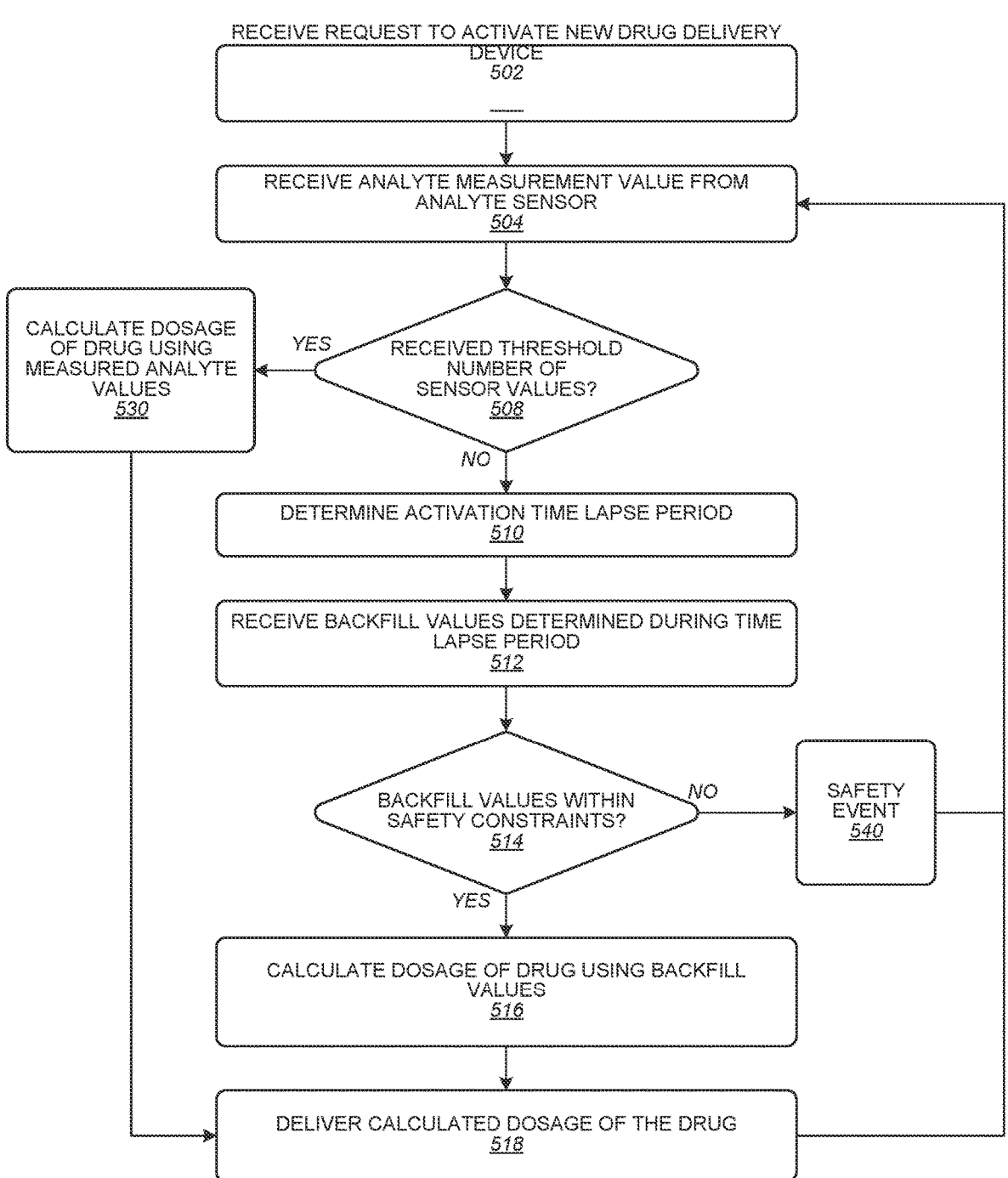
FIG. 5 illustrates a second logic flow in accordance with the present disclosure.

Drug delivery device 160 may also be configured with a processor, a memory, a user interface, a communication device, and/or other components (see, for example, FIG. 5). The memory may store information, such as previous analyte measurement values, delivered drug dosages, and the like. Additionally, the memory may store computer applications, such as a medication delivery application (MDA), automatic analyte control application 166, and the like, that are executable by the processor and configure drug delivery device 160 to perform different functions described in the present disclosure. Drug delivery device 160 may during a cycle be configured to use the present analyte measurement value and information related to the present analyte measurement value to determine a dosage of a drug to be delivered during the cycle. The dosage of the drug may be a basal dosage, a bolus dosage, or a combination of both. "Present analyte measurement value" may refer to the analyte measurement value that is generated by the analyte sensor during a cycle of the drug delivery system. "Information related to the present analyte measurement value" may refer to additional data that is related to the present analyte measurement value such as trend information (i.e., whether the measurement value is increasing, decreasing or level over a period of time), prior analyte measurement values, analyte sensor status (e.g., power level, analyte sensor start date/time, sensor life remaining, or the like) and other information.

In drug delivery system 105, analyte sensor 170 may be configured to provide a present analyte measurement value to the drug delivery device 160. The present analyte measurement value may include information related to the present analyte measurement value as well as information related to past analyte measurement values. For example, when analyte sensor 170 is a continuous glucose monitor (CGM), analyte sensor 170 may be configured to provide a blood glucose measurement value or data indicative of a blood glucose measurement value (for instance, in one non-limiting example, raw data that may be converted into blood glucose values). In addition, analyte sensor 170, when configured as a CGM, may provide a blood glucose trend indication, as well as blood glucose measurement values from one or more past cycles, such as the past two to four cycles. For example, if the CGM is configured to provide a blood glucose measurement value once every 5 minutes (i.e., once every cycle) to drug delivery device 160, the CGM may provide a present analyte measurement value (i.e., a present blood glucose measurement value) at the beginning of a 5-minute cycle as well as past analyte measurement values (i.e., past blood glucose measurement values) from 5 minutes ago and 10 minutes ago. In the example, the present blood glucose measurement value may be provided at time=t(0) and the past blood glucose measurement values may be from time=t(−5) and time=t(−10). The past blood glucose measurement values are obtained at a time prior to the present blood glucose measurement value.

Automatic analyte control application 166 may be configured to receive the respective analyte measurement value from analyte sensor 170 during each respective cycle time, including prior cycle times and the present cycle time. In an operational example, the processors (or processing circuitry) in each of the controller 110, drug delivery device 160 and analyte sensor 170 may be synchronized, for example, based on a common clock or heartbeat. Drug delivery device 160 may be provided with information related to analyte sensor 170 by an application executing on controller 110. For example, a user may input an identifier of analyte sensor 170 into a user interface presented on controller 110. Drug delivery device 160 may receive analyte sensor 170 identifier via communication link 111 from controller 110. Drug delivery device 160 may use analyte sensor 170 identifier to establish communication link 112 with analyte sensor 170. For example, using known handshaking protocols, drug delivery device 160 may provide its identifier to the processor of analyte sensor 170. In some embodiments, analyte measurement values from analyte sensor 170 may be delivered to drug delivery device 160. In other embodiments, analyte measurement values from analyte sensor 170 may be delivered to controller 110.

Using known handshaking protocols or similar procedures, communication link 112 may be established by drug delivery device 160 or analyte sensor 170 at the beginning of each cycle (e.g., preset time period) for a duration long enough to deliver a present analyte measurement value as well as information related to the present analyte measurement value. Once the present analyte measurement value and the information related to the present analyte measurement value are delivered, communication link 112 may be dropped (i.e., disconnected) until the beginning of the next cycle. One purpose of reestablishing communication link 112 at the beginning of every cycle may be to conserve energy for both drug delivery device 160 and analyte sensor 170.

In some embodiments, drug delivery device 160 (or a portion thereof) may need to be exchanged with a new drug delivery device 160. For example, drug delivery device 160 may need to be replaced after a certain time period (for instance, from 24 to 72 hours), after a certain volume of the drug has been dispensed (for instance, about 200 units of insulin), after an indication of a change event, and/or at the discretion of the patient. A non-limiting example of a change event may include an error, empty reservoir (or reservoir volume below a threshold), detection of damage, malfunction, and/or the like.

During the exchange process, drug delivery device 160 may be deactivated and removed from patient 150. A new drug delivery device 160 may be implanted on patient and an activation process may be initiated to prime the new drug delivery device 160 and connect the new drug delivery device 160 components such as analyte sensor 170 and/or controller 110. During this deactivation and initialization phase, drug delivery device 160 may not be able to receive analyte sensor information 134 to perform AAC 166 to provide analyte-based drug delivery. Accordingly, drug delivery device 160 may operate under a standard control 164 process. In some embodiments, standard control 164 may include providing patient 150 with a conservative or "safe" dosage of the drug. For an insulin delivery device, the conservative dosage may be a preset basal dosage, no dosage (for instance, 0 units of insulin), and/or a value between basal and no dosage. In some embodiments, the basal dosage may be a basal dosage determined for the patient during an onboarding process or a basal dosage updated based on patient history with drug delivery system 105.

In some embodiments, patient 150 may initiate a deactivation process for drug delivery device 160 via drug delivery device 160 and/or controller 110 (for instance, via drug delivery management application and user interface 182). A deactivation event or signal may be provided to controller 110 when the deactivation process is initiated. In other embodiments, a deactivation event may be determined based on a lack of communication or other functionality of drug delivery device detected by controller (for instance, patient removes drug delivery device 160 or drug delivery device 160 malfunctions without starting with a deactivation process). Responsive to detecting a deactivation event, controller 110 may establish communication link 113 with analyte sensor 170 (if, for instance, communication link 113 has not already been established). In addition, controller 110 may collect and/or store analyte values measured by analyte sensor as backfill values. In some embodiments, the backfill values may be stored as analyte sensor information 134. In some embodiments, controller may collect and store backfill values from analyte sensor 170 until an activation event is detected. In some embodiments, an activation event may be or may include detection of a new drug delivery device 160 and/or detection that drug delivery device 160 may receive analyte measurements from analyte sensor 170.

During the time window when the previous drug delivery device 160 was deactivated but the new drug delivery device 160 was not activated, controller 110 can continue to receive the analyte values measured by analyte sensor by connecting over its own communication link 113 and sending or using this information immediately after activation of the new drug delivery device 160 for automated control of drug delivery via drug delivery device 160 (for instance, via AAC 166).

Figure 2:
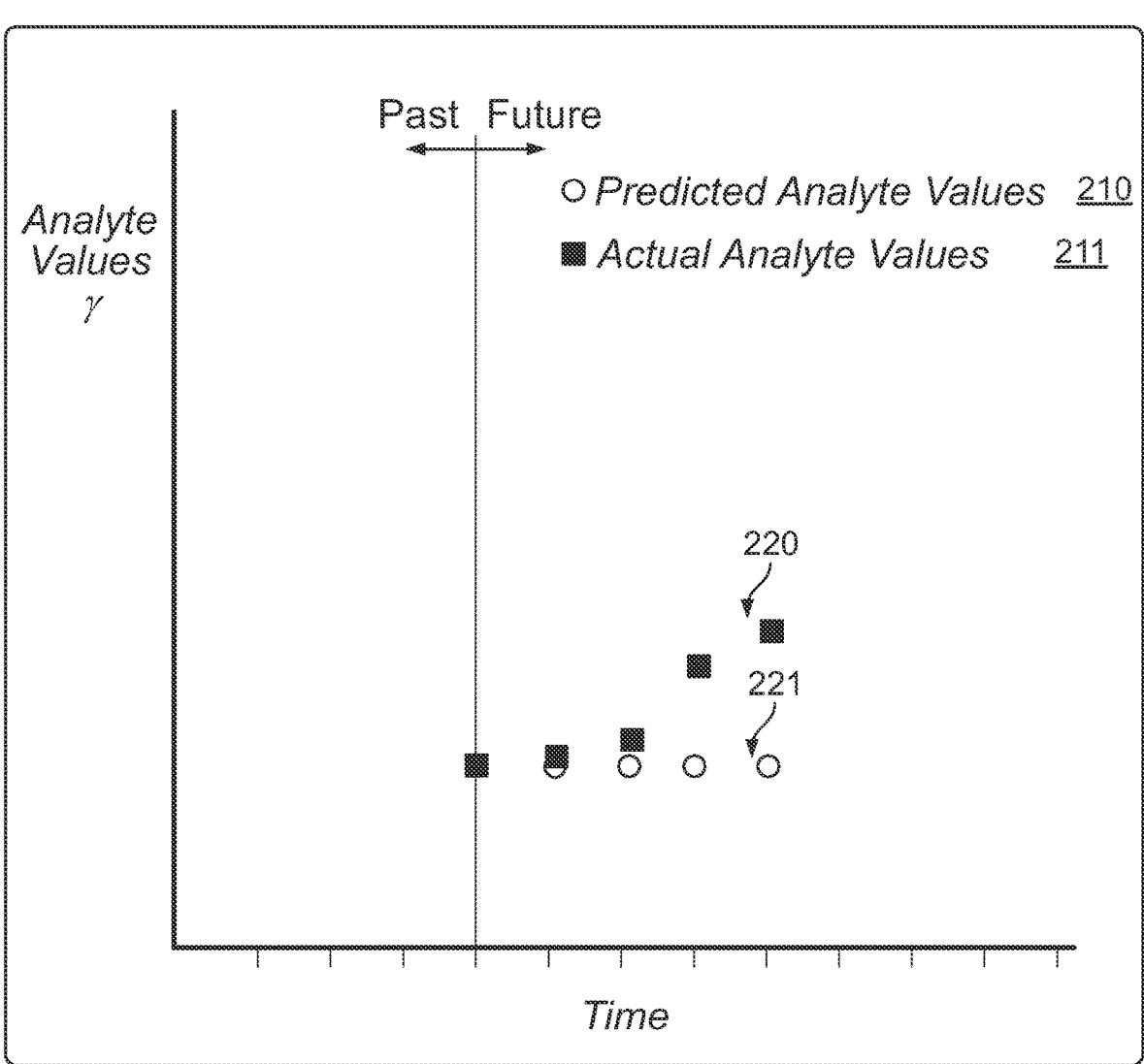
FIG. 2 illustrates a graph of actual and predicted analyte values in accordance with the present disclosure.

FIG. 2 illustrates a graph of actual and predicted analyte values in accordance with the present disclosure and FIG. 3 illustrates a graph of backfill, actual, and predicted analyte values in accordance with the present disclosure. Referring to FIG. 2, therein is provided a graph 205 of analyte values versus time. In a situation in which drug delivery device 160 does not have previous analyte values, for example, upon activation using conventional devices and processes, the predicted analyte values 210 may be a flat initial predicted trend due to a lack of backfill values. For example, trend line 221 (or trend points) may be an extension of an initial analyte value received from analyte sensor 170 when drug delivery device 160 becomes activated and is able to receive analyte values. For example, conventional drug delivery devices, such as AID devices, may assume that the initial input CGM value has been maintained at a constant value, and initiates or establishes a predicted glucose trend as a flat trajectory with the first input CGM value received during initialization. As this is not patient's 150 true CGM trend, it is not safe to deliver insulin based on this trajectory immediately, and the system typically delivers a conservative value (e.g., a preset basal rate).

As indicated in FIG. 2, the plot of actual analyte values 220 may be materially higher. However, without using backfill values according to some embodiments upon activation, drug delivery device 160 (and AAC 166) may follow a conservative approach and provide insulin according to trend line 221 instead of actual values 220. Accordingly, patient 150 may not receive proper treatment based on their actual analyte values during this "warm-up," blanking, or initialization period.

Referring now to FIG. 3, some embodiments may collect, access, or otherwise receive backfill analyte values 312. In various embodiments, backfill analyte values 312 may be used to generate predicted analyte values 311 when drug delivery device 160 becomes activated. Backfill analyte values 312 may be used to generate a trend 321 (or trend points) of predicted analyte values 311 that more closely matches actual analyte values 310 of patient 150.

For example, certain commercial analyte sensors may have the capability to provide "backfill" analyte values (for instance, when stored locally in a memory) when communication is established. In another example, controller 110 may store analyte values that may be used as backfill values. Drug delivery system 105 can deliver a drug based on a trend calculated from these backfill values, avoiding the need for a more conservative starting period over several minutes. In this manner, analyte-based drug delivery processes according to some embodiments may provide better treatment to patient 150.

Future analyte values may be predicted based on prior analyte values. For example, for an insulin delivery device, future glucose values may be predicted based on prior glucose measurement values (for instance, trend 320). An insulin basal delivery rate may be determined or adjusted to be provided by an insulin delivery device based on the predicted future glucose values. Insulin may be delivered via the insulin delivery device according to the adjusted insulin basal delivery rate. Predictions of future glucose values or trends based on backfill values and/or the determination of insulin delivery dosages based on predictions of future glucose values based on backfill values may be determined according to various processes. Non-limiting examples of prediction and/or dosing processes for insulin may include all or some of U.S. patent application Ser. No. 16/586,499, entitled "Onboarding and Total Daily Insulin Adaptivity;" Ser. No. 16/402,753, entitled "Safety Constraints for a Control Algorithm Based Drug Delivery System;" and/or Ser. No. 17/112,314, entitled "Techniques and Devices Providing Adaptivity and Personalization in Diabetes Treatment;" each of which is incorporated by reference as if fully set forth in this present disclosure.

If initial analyte values are not available at the time of activation, processes according to some embodiments may use stratification based upon missing points from any prior analyte point or backfill information. In various embodiments, analyte-based drug delivery control may assess if the suggested delivery based on stratification compared to the conservative approach of basal and delivers and determine delivery dosages accordingly. For example, for an insulin delivery device, if blood glucose was dropping before the deactivation event (or the sensor and drug delivery device otherwise lose communication), then the analyte-based drug delivery process (i.e., AAC) may determine that glucose will, for instance, continue to drop, at least for a period of time, taking into account past trends. Accordingly, as the analyte-based drug delivery process continues to miss points, the process may determine what occurred in the past via the backfill values and determine a trend. For instance, analyte-based drug delivery process may perform a stratified missing point compensation process for points or other information missing due to the deactivation/initialization process. A non-limiting example of a stratified missing point compensation process may include processes the same or similar to the subject matter disclosed in U.S. Provisional Patent Application Ser. No. 63/158,643, entitled "Opportunistic Retrieval of Analyte Value to Improve Automatic Drug Control Accuracy," which is incorporated by reference as if fully set forth in this present disclosure.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 4:
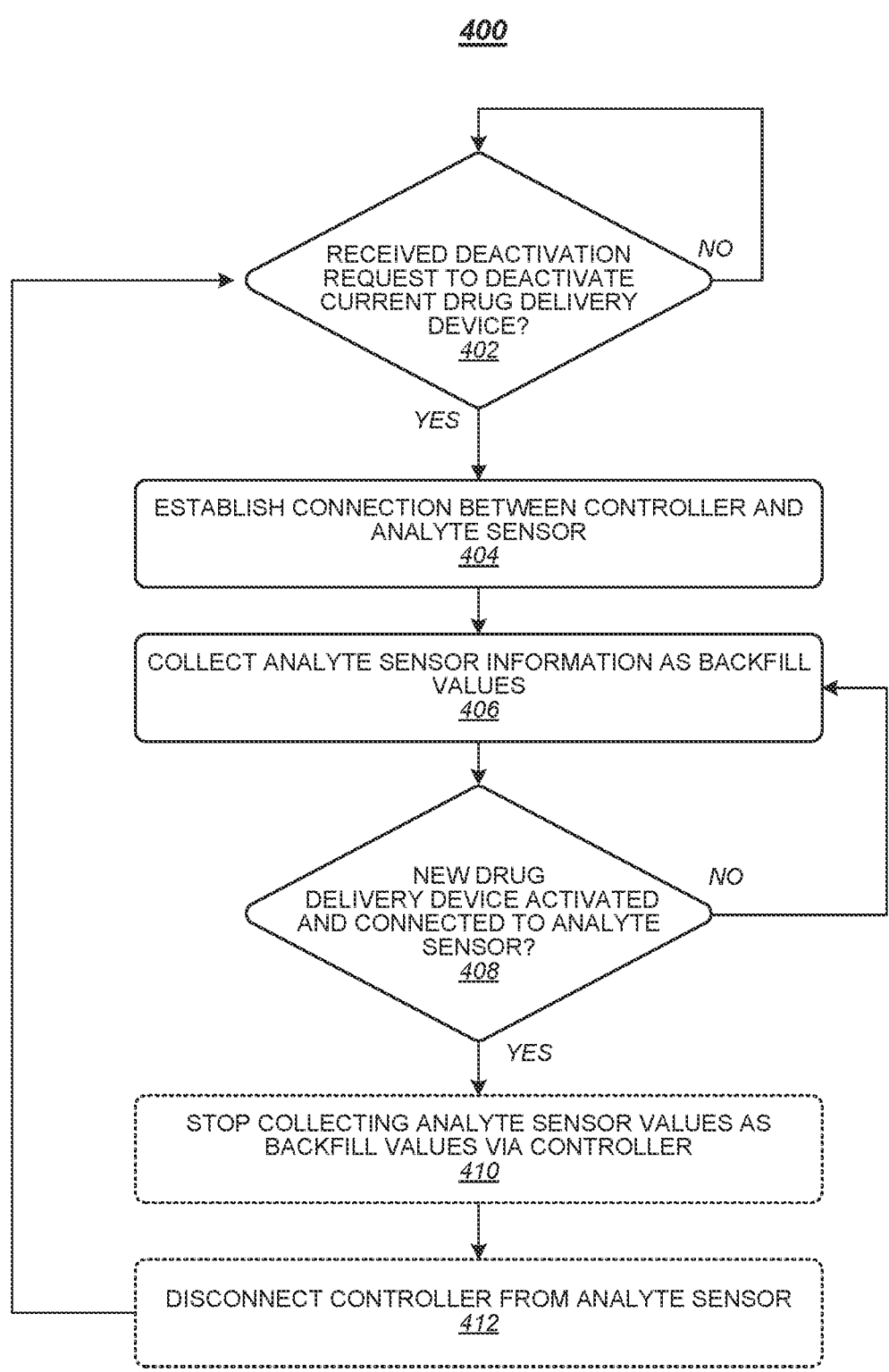
FIG. 4 illustrates a first logic flow in accordance with the present disclosure.

FIG. 4 illustrates an embodiment of a logic flow 400. Logic flow 400 may be representative of some or all of the operations executed by one or more embodiments described herein, such as devices of operating environment 100 and/or 600. For example, logic flow 400 may be a process performed by controller 110 of FIG. 1.

At block 402, logic flow 400 may determine whether a deactivation request has been received. For example, controller 110 may receive or determine that patient 150 (or another user) has initiated deactivation of drug delivery device 160. In some embodiments, a direct deactivation may not be required at block 402. For example, block 402 may cause logic flow to move to block 404 responsive to a loss of communication or other functionality of a drug delivery device. Logic flow 400 may cause a controller (or other logic device) to establish a connection with an analyte sensor. For example, controller 110 may establish a communication link 113 with analyte sensor 170. At block 406, logic flow 400 may collect analyte sensor information as backfill values. For example, controller 110 may receive analyte values measured via analyte sensor 170 over communication link 113. The analyte values may be stored as backfill values in analyte sensor information 134.

At block 408, logic flow 400 may determine whether a new drug delivery device has been activated and connected to the analyte sensor. For example, controller 110 may receive a signal indicating or otherwise determine that a new drug delivery device 160 has been activated and is receiving analyte values from analyte sensor 170.

In some embodiments, logic flow 400 may cause the controller to stop collecting analyte values from analyte sensor as backfill values at block 410. In various embodiments, at block 412, logic flow 400 may disconnect controller from analyte sensor, for instance, by disconnecting communication link 113 between controller 110 and analyte sensor 170.

FIG. 5 illustrates an embodiment of a logic flow 500. Logic flow 500 may be representative of some or all of the operations executed by one or more embodiments described herein, such as devices of operating environment 100 and/or 600.

At block 502, logic flow 500 may receive a request to activate a new drug delivery device. For example, a new drug delivery device 160 may be installed on patient and may start an initiation process. Logic flow 500 may receive an analyte measurement value from an analyte sensor at block 504. For instance, (new) drug delivery device 160 may receive an analyte value measured by analyte sensor 170. At block 508, logic flow 500 may determine whether a threshold number of sensor values has been received. For example, an AAC process for controlling drug delivery via drug delivery device 160 may operate based on analyte values, trends, and/or the like. The AAC process may require a certain number, amount, or other threshold of analyte values to use as a basis for drug delivery. For example, the threshold may be a certain number of (continuous or semi-continuous) measured analyte values, such as 2 values, 3 values, 4 values, 5 values, 10 values, 20 values, 30 values, 100 values, and any value or range between any two of these values (including endpoints). In another example, the threshold may be based on a time period of value measurement, such as 1 minute, 5 minutes, 10 minutes, 15 minutes, 20 minutes, 30 minutes, 60 minutes, and any value or range between any two of these values (including endpoints). In a further example, the threshold may be based on a number of cycles, such as 1 cycle, 3 cycles, 5 cycles, 10 cycles, and any value or range between any two of these values (including endpoints).

If the threshold number of sensor values has been received by the drug delivery device 160, logic flow 500 may calculate the dosage of the drug using the measured analyte values at block 530. If the threshold number of sensor values has not been received by the drug delivery device 160, logic flow 500 may determine an activation time lapse period at block 510. In some embodiments, the time lapse period may be a time period between when the previous drug delivery device 160 was deactivated and the new drug delivery device 160 was activated (and/or received a first analyte value from analyte sensor 170). In general, in various embodiments, the time lapse value may be a time period or duration thereof in which a drug delivery device was inactive.

At block 512, logic flow 500 may receive backfill values determined during the time lapse period. For example, controller 110 may store or may access backfill values measured by analyte sensor 170 while drug delivery device 160 was inactive and/or not receiving analyte values from analyte sensor 170. The number and/or duration of backfill values may be determined based on the amount of available backfill values. In various embodiments, the number of backfill values may be a threshold number of backfill values, such as 2 values, 3 values, 4 values, 5 values, 10 values, 20 values, 30 values, 100 values, and any value or range between any two of these values (including endpoints). In another example, the threshold duration of backfill values may be based on a time period, such as 1 minute, 5 minutes, 10 minutes, 15 minutes, 20 minutes, 30 minutes, 60 minutes, and any value or range between any two of these values (including endpoints). In a further example, the threshold may be based on a number of cycles, such as 1 cycle, 3 cycles, 5 cycles, 10 cycles, and any value or range between any two of these values (including endpoints).

In general, the threshold of backfill values may be required to ensure there is a sufficient amount of backfill values to determine trends and/or the like for use by an AAC process to deliver a drug based, at least in part, on the backfill values. In some embodiments, backfill values may be used over a duration that precedes the time lapse period (for instance, the time lapse period may be 5 minutes and backfill values measured 10 minutes prior may also be used alone or along with those measured during the time lapse period).

At block 514, logic flow 500 may determine whether the backfill values are within safety constraints. For example, a correlation safety constraint may be based on whether measured analyte values received when the new drug delivery device 160 is activated and starts receiving values is within a correlation threshold of the backfill values. For instance, a correlation threshold for an analyte may be a concentration of 20 mg/dL (or other units as appropriate, such as units/liter). If a first analyte value is (or threshold number of first values are) determined to be 20 mg/dL different from the backfill values (or a specific range of backfill values, such as the last five values), then a safety event may be triggered at block 540 and the backfill values are not used to determine a drug delivery dosage (for example, the first value is 10 units/liter and the last five backfill values average 40 units/liter). In various embodiments, a safety constraint may include requiring a sufficient number and/or continuous number of backfill values. For example, if there is an insufficient number of backfill values (for instance, between less than 10 and less than 2) or if there is too long of a duration of missing backfill values (for instance, between 1 minute and 10 minutes between consecutive backfill values), a safety event may be triggered.

In some embodiments, a safety event may cause a default amount of the drug dosage to be used (for instance, a preset basal amount, less than a preset or historical basal amount, no volume of the drug, and/or the like). In various embodiments, a safety event may cause an alert or other message to be presented to patient 150 or another user, for example, for manual analyte measurement and drug delivery.

Logic flow 500 may calculate a dosage of the drug using the backfill values at block 516. For example, referring to FIG. 3, logic flow 500 may use backfill values 312 to determine a future trend line 321 in combination with one or more first analyte values after activation of a new drug delivery device. Future trend line 321 may be used, for instance, by an AAC process to determine a drug dosage.

In some embodiments, the calculated dosage may be based on a conservative, preset basal dosage. For example, logic flow 500 may determine a confidence level associated with the backfill values. In some embodiments, the calculated dosage may be a multiple or add-on to a preset or a historical basal dosage (e.g., a historical average basal dosage) (in either case, hereafter "basal") depending on a confidence level in the backfill values. For instance, for a confidence level of X, the calculated dosage may be (basal) $*(1.10)$. In another instance, for a confidence level of Y, the calculated dosage may be (basal)$*(0.5)$. In some embodiments, if the confidence level is above a confidence threshold value, the calculated dosage may be based on a prediction processes described in the present disclosure. In other embodiments, if the confidence level is below the confidence threshold value, the calculated dosage may be based on the basal value.

At block 518, logic flow 500 may cause the calculated dosage of the drug to be delivered to the patient.

Figure 6:
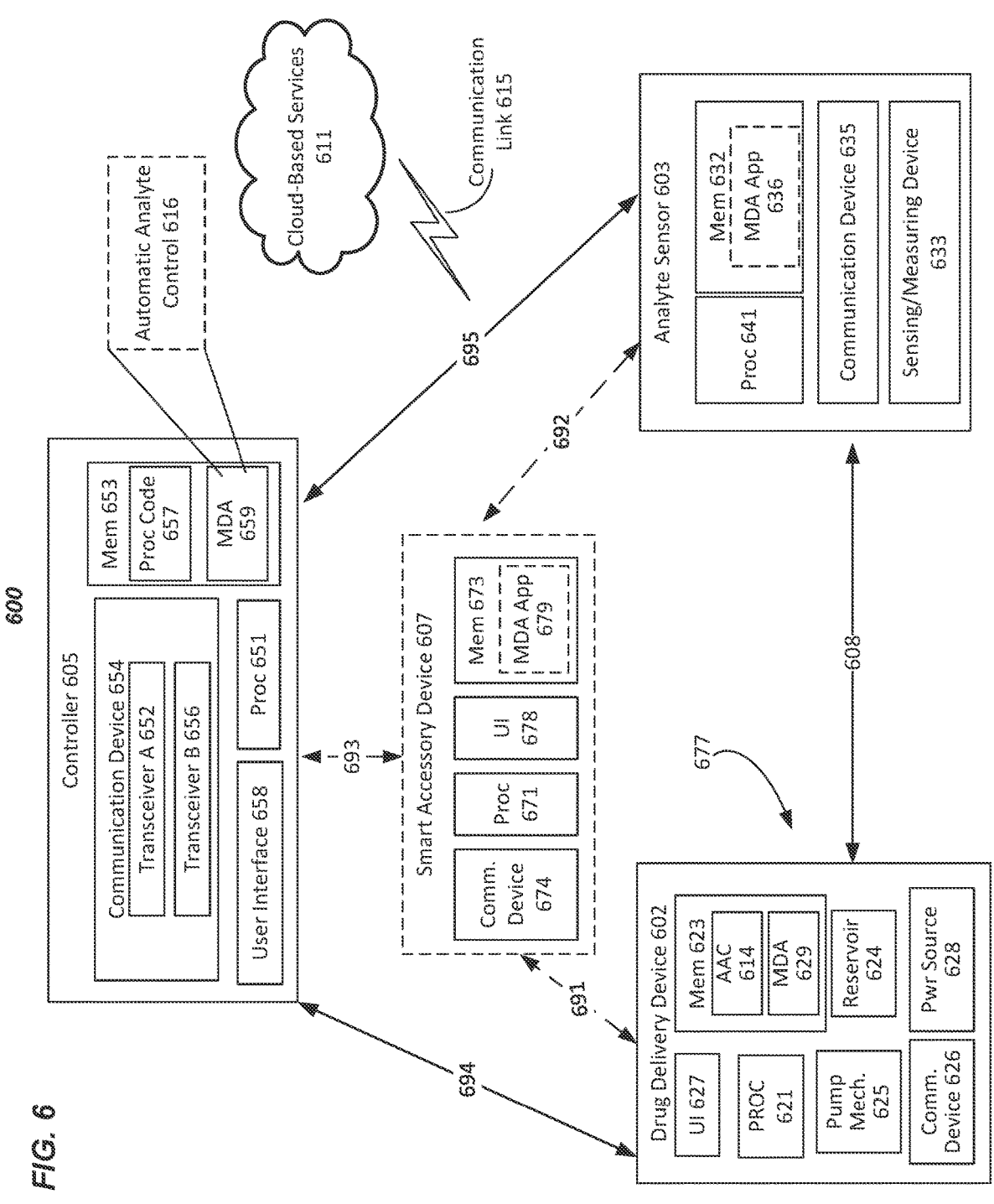
FIG. 6 illustrates a functional block diagram of a system in accordance with the present disclosure.

FIG. 6 illustrates a functional block diagram of a system example suitable for implementing the example processes and techniques described herein.

The operating environment 600 may be or may include an automatic drug delivery system that may include components such as an automatic drug delivery system that is configured to determine a drug dosage and deliver the dosage of the drug without any user interaction, or in some examples, limited user interaction, such as in response to a user depressing a button to indicate measurement of blood glucose or another analyte, or the like. "Drug delivery system environment" may refer to a computing and sensing environment that includes cloud based services, a drug delivery system (that may include a controller, a drug delivery device, and an analyte sensor) and optionally additional devices. The components of the drug delivery system environment may cooperate to provide present analyte measurement values or at least accurate estimates of present analyte measurement values to facilitate calculation of optimal drug dosages for a user.

The automatic drug delivery system 600 may implement (and/or provide functionality for) a medication delivery algorithm, such as an artificial pancreas (AP) application, to govern or control automated delivery of a drug or medication, such as insulin, to a user (e.g., to maintain euglycemia—a normal level of glucose in the blood). The drug delivery system 600 may be an automated drug delivery system that may include a wearable automatic drug delivery device 602, an analyte sensor 603, and a management device (for instance, a PDM, smart phone, table computing device, and/or the like) 605.

The system 600, in an optional example, may also include a smart accessory device 607, such as a smartwatch, a personal assistant device or the like, which may communicate with the other components of system 600 via either a wired or wireless communication links 691-693.

The management device 605 may be a computing device such as a smart phone, a tablet, a personal diabetes management device, a dedicated diabetes therapy management device, or the like. In an example, the management device (PDM) 605 may include a processor 651, a management device memory 653, a user interface 658, and a communication device 654. The management device 605 may contain analog and/or digital circuitry that may be implemented as a processor 651 for executing processes based on programming code stored in the management device memory 653, such as the medication delivery algorithm or application (MDA) 659, to manage a user's blood glucose levels and for controlling the delivery of the drug, medication, or therapeutic agent to the user as well as other functions, such as calculating carbohydrate-compensation dosage, a correction bolus dosage and the like as discussed above. The management device 605 may be used to program, adjust settings, and/or control operation of the wearable automatic drug delivery device 602 and/or the analyte sensor 603 as well as the optional smart accessory device 607.

The processor 651 may also be configured to execute programming code stored in the management device memory 653, such as the MDA 659. The MDA 659 may be a computer application that is operable to deliver a drug based on information received from the analyte sensor 603, the cloud-based services 611 and/or the management device 605 or optional smart accessory device 607. The memory 653 may also store programming code to, for example, operate the user interface 658 (e.g., a touchscreen device, a camera or the like), the communication device 654 and the like. The processor 651 when executing the MDA 659 may be configured to implement indications and notifications related to meal ingestion, blood glucose measurements, and the like. The user interface 658 may be under the control of the processor 651 and be configured to present a graphical user interface that enables the input of a meal announcement, adjust setting selections and the like as described above.

In a specific example, when the MDA 659 is an artificial pancreas (AP) application, the processor 651 is also configured to execute a diabetes treatment plan (which may be stored in a memory) that is managed by the MDA 659 stored in memory 653. In addition to the functions mentioned above, when the MDA 659 is an AP application, it may further provide functionality to enable the processor 651 to determine a carbohydrate-compensation dosage, a correction bolus dosage and determine a basal dosage according to a diabetes treatment plan. In addition, as an AP application, the MDA 659 provides functionality to enable the processor 651 to output signals to the wearable automatic drug delivery device 602 to deliver the determined bolus and basal dosages described with reference to the examples of FIGS. 1-4.

The communication device 654 may include one or more transceivers such as Transceiver A 652 and Transceiver B 656 and receivers or transmitters that operate according to one or more radio-frequency protocols. In the example, the transceivers 652 and 656 may be a cellular transceiver and a Bluetooth® transceiver, respectively. For example, the communication device 654 may include a transceiver 652 or 656 configured to receive and transmit signals containing information usable by the MDA 659.

The wearable automatic drug delivery device 602, in the example system 600, may include a user interface 627, a controller 621, a drive mechanism 625, a communication device 626, a memory 623, a power source/energy harvesting circuit 628, device sensors 684, and a reservoir 624. The wearable automatic drug delivery device 602 may be configured to perform and execute the processes described in the examples of FIGS. 4 and 5 without input from the management device 605 or the optional smart accessory device 607. As explained in more detail, the controller 621 may be operable, for example, implement the processes of FIGS. 4 and 5 as well as determine an amount of insulin delivered, JOB, insulin remaining, and the like. The controller 621 alone may implement the processes of FIGS. 4 and 5 as well as determine an amount of insulin delivered, JOB, insulin remaining, and the like, such as control insulin delivery, based on an input from the analyte sensor 604.

The memory 623 may store programming code executable by the controller 621. The programming code, for example, may enable the controller 621 to control expelling insulin from the reservoir 624 and control the administering of doses of medication based on signals from the MDA 629 or, external devices, if the MDA 629 is configured to implement the external control signals.

The reservoir 624 may be configured to store drugs, medications or therapeutic agents suitable for automated delivery, such as insulin, morphine, blood pressure medicines, chemotherapy drugs, or the like.

The device sensors 684 may include one or more of a pressure sensor, a power sensor, or the like that are communicatively coupled to the controller 621 and provide various signals. For example, the pressure sensor may be coupled to or integral with a needle/cannula insertion component (which may be part of the drive mechanism 625) or the like. In an example, the controller 621 or a processor, such as 651, may be operable to determine that a rate of drug infusion based on the indication of the fluid pressure. The rate of drug infusion may be compared to an infusion rate threshold, and the comparison result may be usable in determining an amount of insulin onboard (JOB) or a total daily insulin (TDI) amount.

In an example, the wearable automatic drug delivery device 602 includes a communication device 626, which may be a receiver, a transmitter, or a transceiver that operates according to one or more radio-frequency protocols, such as Bluetooth, Wi-Fi, a near-field communication standard, a cellular standard, or the like. The controller 621 may, for example, communicate with a personal diabetes management device 605 and an analyte sensor 603 via the communication device 626.

The wearable automatic drug delivery device 602 may be attached to the body of a user, such as a patient or diabetic, at an attachment location and may deliver any therapeutic agent, including any drug or medicine, such as insulin or the like, to a user at or around the attachment location. A surface of the wearable automatic drug delivery device 602 may include an adhesive to facilitate attachment to the skin of a user as described in earlier examples.

The wearable automatic drug delivery device 602 may, for example, include a reservoir 624 for storing the drug (such as insulin), a needle or cannula (not shown in this example) for delivering the drug into the body of the user (which may be done subcutaneously, intraperitoneally, or intravenously), and a drive mechanism 625 for transferring the drug from the reservoir 624 through a needle or cannula and into the user. The drive mechanism 625 may be fluidly coupled to reservoir 624, and communicatively coupled to the controller 621.

The wearable automatic drug delivery device 602 may further include a power source 628, such as a battery, a piezoelectric device, other forms of energy harvesting devices, or the like, for supplying electrical power to the drive mechanism 625 and/or other components (such as the controller 621, memory 623, and the communication device 626) of the wearable automatic drug delivery device 602.

In some examples, the wearable automatic drug delivery device 602 and/or the management device 605 may include a user interface 658, respectively, such as a keypad, a touchscreen display, levers, light-emitting diodes, buttons on a housing of the management device 605, a microphone, a camera, a speaker, a display, or the like, that is configured to allow a user to enter information and allow the management device 605 to output information for presentation to the user (e.g., alarm signals or the like). The user interface 658 may provide inputs, such as a voice input, a gesture (e.g., hand or facial) input to a camera, swipes to a touchscreen, or the like, to processor 651 which the programming code interprets.

When configured to communicate to an external device, such as the PDM 605 or the analyte sensor 604, the wearable automatic drug delivery device 602 may receive signals over the wired or wireless link 694 from the management device (PDM) 605 or 608 from the analyte sensor 604. The controller 621 of the wearable automatic drug delivery device 602 may receive and process the signals from the respective external devices as described with reference to the examples of FIGS. 4 and 5 as well as implementing delivery of a drug to the user according to a diabetes treatment plan or other drug delivery regimen.

In an operational example, the processor 621 when executing the MDA 659 may output a control signal operable to actuate the drive mechanism 625 to deliver a carbohydrate-compensation dosage of insulin, a correction bolus, a revised basal dosage or the like as described with reference to the examples of FIGS. 4 and 5.

The smart accessory device 607 may be, for example, an Apple Watch®, other wearable smart device, including eyeglasses, provided by other manufacturers, a global positioning system-enabled wearable, a wearable fitness device, smart clothing, or the like. Similar to the management device 605, the smart accessory device 607 may also be configured to perform various functions including controlling the wearable automatic drug delivery device 602. For example, the smart accessory device 607 may include a communication device 674, a processor 671, a user interface 678 and a memory 673. The user interface 678 may be a graphical user interface presented on a touchscreen display of the smart accessory device 607. The memory 673 may store programming code to operate different functions of the smart accessory device 607 as well as an instance of the MDA 679. The processor 671 that may execute programming code, such as site MDA 679 for controlling the wearable automatic drug delivery device 602 to implement the FIGS. 4 and 5 examples described herein.

The analyte sensor 603 may include a controller 631, a memory 632, a sensing/measuring device 633, a user interface 637, a power source/energy harvesting circuitry 634, and a communication device 635. The analyte sensor 603 may be communicatively coupled to the processor 651 of the management device 605 or controller 621 of the wearable automatic drug delivery device 602. The memory 632 may be configured to store information and programming code, such as an instance of the MDA 636.

The analyte sensor 603 may be configured to detect multiple different analytes, such as lactate, ketones, uric acid, sodium, potassium, alcohol levels or the like, and output results of the detections, such as measurement values or the like. The analyte sensor 603 may, in an example, be configured to measure a blood glucose value at a predetermined time interval, such as every 5 minutes, every cycle, or the like. The communication device 635 of analyte sensor 603 may have circuitry that operates as a transceiver for communicating the measured blood glucose values to the management device 605 over a wireless link 695 or with wearable automatic drug delivery device 602 over the wireless communication link 608. While called an analyte sensor 603, the sensing/measuring device 633 of the analyte sensor 603 may include one or more additional sensing elements, such as a glucose measurement element a heart rate monitor, a pressure sensor, or the like. The controller 631 may include discrete, specialized logic and/or components, an application-specific integrated circuit, a microcontroller or processor that executes software instructions, firmware, programming instructions stored in memory (such as memory 632), or any combination thereof.

Similar to the controller 621, the controller 631 of the analyte sensor 603 may be operable to perform many functions. For example, the controller 631 may be configured by the programming code stored in the memory 632 to manage the collection and analysis of data detected the sensing and measuring device 633.

Although the analyte sensor 603 is depicted in FIG. 6 as separate from the wearable automatic drug delivery device 602, in various examples, the analyte sensor 603 and wearable automatic drug delivery device 602 may be incorporated into the same unit. That is, in various examples, the sensor 603 may be a part of the wearable automatic drug delivery device 602 and contained within the same housing of the wearable automatic drug delivery device 602 (e.g., the sensor 603 or, only the sensing/measuring device 633 and memory storing related programming code may be positioned within or integrated into, or into one or more components, such as the memory 623, of, the wearable automatic drug delivery device 602). In such an example configuration, the controller 621 may be able to implement the process examples of FIGS. 4 and 5 alone without any external inputs from the management device 605, the cloud-based services 611, another sensor (not shown), the optional smart accessory device 607, or the like.

The communication link 615 that couples the cloud-based services 611 to the respective devices 602, 603, 605 or 607 of system 600 may be a cellular link, a Wi-Fi link, a Bluetooth link, or a combination thereof. Services provided by cloud-based services 611 may include data storage that stores anonymized data, such as blood glucose measurement values, historical IOB or TDI, prior carbohydrate-compensation dosage, and other forms of data. In addition, the cloud-based services 611 may process the anonymized data from multiple users to provide generalized information related to TDI, insulin sensitivity, IOB and the like.

The wireless communication links 608, 691, 692, 693, 694 and 695 may be any type of wireless link operating using known wireless communication standards or proprietary standards. As an example, the wireless communication links 608, 691, 692, 693, 694 and 695 may provide communication links based on Bluetooth®, Zigbee®, Wi-Fi, a near-field communication standard, a cellular standard, or any other wireless protocol via the respective communication devices 654, 674, 626 and 635.

Software related implementations of the techniques described herein, such as the processes examples described with reference to FIGS. 4 and 5 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts requesting the input of information such as weight or age. Similarly, a dosage amount of insulin may be received by the AP application or algorithm from a user via a user interface. Other open-loop actions may also be implemented by adjusting user settings or the like in an AP application or algorithm.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

The invention claimed is:

1. A drug delivery device, comprising:
a processor; and
a memory storing instructions that, when executed by the processor, operate the drug delivery device to:
receive a present analyte measurement value from an analyte sensor during an initialization of the drug delivery device, wherein the initialization is associated with an exchange of the drug delivery device for a deactivated drug delivery device,
receive at least one backfill value measured by the analyte sensor prior to the initialization,
calculate a dosage of a drug using the present analyte measurement value and the at least one backfill value, and
deliver the dosage of the drug.

2. The drug delivery device of claim 1, the at least one backfill value comprising:
a plurality of analyte values determined by the analyte sensor prior to the initialization of the drug delivery device, or
a plurality of analyte values stored by an external controller prior to the initialization of the drug delivery device.

3. The drug delivery device of claim 1, the instructions, when executed by the processor, to operate the drug delivery device to determine an analyte concentration trend based on the present analyte measurement value and the at least one backfill value, and to calculate the dosage based on the analyte concentration trend.

4. The drug delivery device of claim 1, the instructions, when executed by the processor, to operate the drug delivery device to receive the at least one backfill value from a controller located external to the drug delivery device.

5. The drug delivery device of claim 1, the instructions, when executed by the processor, to operate the drug delivery device to determine whether the at least one backfill value meets a safety constraint that comprises:
a minimum number of values in the at least one backfill value, or
the at least one backfill value being within a correlation threshold of the present analyte measurement value.

6. The drug delivery device of claim 1, wherein the analyte measurement value is a blood glucose measurement value, and the drug is insulin, glucagon, a glucagon-like peptide or a combination of at least two of insulin, glucagon or the glucagon-like peptide.

7. A system comprising:
the drug delivery device of claim 1, wherein the drug delivery device is a first drug delivery device, and further comprising:
a controller configured to:
receive a deactivation indication from the first drug delivery device that the first drug delivery device is being deactivated, establish a connection to a sensor device responsive to the deactivation indication, and
collect sensor measurement values from the sensor device as backfill values.

8. The system of claim 7, wherein the controller is further configured to:
receive an initialization indication from a second drug delivery device that the second drug delivery device is being initialized, and
provide the at least one backfill value to the second drug delivery device.

9. A computer-implemented method of operating a drug delivery device, comprising:
receiving a present analyte measurement value from an analyte sensor during an initialization of the drug delivery device, wherein the initialization is associated with an exchange of the drug delivery device for a deactivated drug delivery device;
receiving at least one backfill value measured by the analyte sensor prior to the initialization;
calculating, via a processor of the drug delivery device, a dosage of a drug using the present analyte measurement value and the at least one backfill value; and
delivering the dosage of the drug.

10. The computer-implemented method of claim 9, the at least one backfill value comprising:
a plurality of analyte values determined by the analyte sensor prior to the initialization of the drug delivery device, or
a plurality of analyte values stored by an external controller prior to the initialization of the drug delivery device.

11. The computer-implemented method of claim 9, further comprising operating the drug delivery device to determine an analyte concentration trend based on the present analyte measurement value and the at least one backfill value, and to calculate the dosage based on the analyte concentration trend.

12. The computer-implemented method of claim 9, further comprising operating the drug delivery device to receive the at least one backfill value from a controller located external to the drug delivery device.

13. The computer-implemented method of claim 9, further comprising operating the drug delivery device to determine whether the at least one backfill value meets a safety constraint that comprises:
a minimum number of values in the at least one backfill value, or
the at least one backfill value being within a correlation threshold of the present analyte measurement value.

14. The computer-implemented method of claim 9, wherein the analyte measurement value is a blood glucose measurement value, and the drug is insulin, glucagon, a glucagon-like peptide or a combination of at least two of insulin, glucagon or the glucagon-like peptide.

15. The computer-implemented method of claim 9, wherein the drug delivery device is a first drug delivery device, and further comprising:
receiving a deactivation indication from the first drug delivery device that the first drug delivery device is being deactivated,
establishing a connection to a sensor device responsive to the deactivation indication, and
collecting sensor measurement values from the sensor device as backfill values.

16. The computer-implemented method of claim 15, further comprising:

receiving an initialization indication from a second drug delivery device that the second drug delivery device is being initialized, and providing the at least one backfill value to the second drug delivery device.

\* \* \* \* \*